United States Patent
Phelps et al.

(10) Patent No.: US 10,822,584 B2
(45) Date of Patent: Nov. 3, 2020

(54) PELLETS USED IN CELL CULTURE AND METHODS OF MAKING THEREOF

(71) Applicant: Life Technologies Corporation, Carlsbad, CA (US)

(72) Inventors: Mwita Phelps, Buffalo, NY (US); Paul Gulde, Clarence Center, NY (US); Richard Fike, Clarence, NY (US); Mary Reynolds, North Tonawanda, NY (US); Richard Hassett, Tonawanda, NE (US); Andrew Campbell, Tonawanda, NY (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 15/566,899

(22) PCT Filed: Dec. 16, 2016

(86) PCT No.: PCT/US2016/067374
§ 371 (c)(1),
(2) Date: Oct. 16, 2017

(87) PCT Pub. No.: WO2017/106783
PCT Pub. Date: Jun. 22, 2017

(65) Prior Publication Data
US 2018/0142203 A1 May 24, 2018

Related U.S. Application Data

(60) Provisional application No. 62/269,031, filed on Dec. 17, 2015.

(51) Int. Cl.
*C12N 5/00* (2006.01)
*C12N 1/22* (2006.01)
*B01J 8/18* (2006.01)

(52) U.S. Cl.
CPC .......... *C12N 5/0018* (2013.01); *B01J 8/1845* (2013.01); *C12N 1/22* (2013.01); *C12N 2500/32* (2013.01); *C12N 2500/34* (2013.01); *C12N 2500/60* (2013.01)

(58) Field of Classification Search
CPC ...................................................... C12N 1/22
See application file for complete search history.

(56) References Cited

U.S. PATENT DOCUMENTS 4,858,552 A    8/1989  Glatt et al.
4,962,091 A *  10/1990 Eppstein ............ A61K 9/1647
                                               424/130.1
2008/0019883 A1   1/2008  Fike et al.
2013/0267027 A1  10/2013  Rayner-Brandes et al.
2014/0273205 A1*  9/2014  Price ........................ C12N 5/06
                                               435/348

FOREIGN PATENT DOCUMENTS

EP      2281873 A1      2/2011
JP      H0257175 A      2/1990
WO      WO-2014025514 A1  2/2014

OTHER PUBLICATIONS

Korakianiti et al. AAPS PharmSciTech., 2000, 1(4) article 35 pp. 1-5.*
Kleinebudde et al. Handbook of Powder Technology, Dec. 2007, 11:779-811. Chapter 17 Direct pelletization of pharmaceutical pellets in fluid-bed processes.*
Fike R., et al., "Advanced Granulation Technology (AGT TM), An Alternate Format for Serum-Free, Chemically-Defined and Protein-Free Culture Media," Cytotechnology, Kluwer Academic Publishers (2001), vol. 36, pp. 33-39.
Glatt: "Fluid Bed Systems", Apr. 1, 2005 (Apr. 1, 2005), XP055340948, 20 pages, Retrieved from the Internet: URL:http://www.glatt.com/fileadmin/user_upload/content/pdf_downloads/WS_EN_7221_301.pdf [retrieved on Feb. 1, 2017].
International Search Report and Written Opinion for Application No. PCT/US2016/067374, dated Mar. 29, 2017, 18 pages.
Korakianiti E S., et al., "Optimization of the Pelletization Process in a Fluid-Bed Rotor Granulator Using Experimental Design," AAPS PharmSciTech, vol. 1, No. 4, Dec. 1, 2000 (Dec. 1, 2000), pp. 71-75, DOI:10.1208/pt010435.
Anonymous: "Spray Granulation Agglomeration Coating Pelletizing Innovative Technologies for Granules and Pellets", Oct. 17, 2011 (Oct. 17, 2011), XP055355183, Retrieved from the Internet: URL:https://web.archive.org/web/20141222051811/http://www.glatt.com/fileadmin/user_upload/content/pdf_downloads/AB_innovative_technologies_en_11101 . . . [retrieved on Mar. 15, 2017].
SG11201805049, Search Report, dated Aug. 5, 2019, 4 pages.

* cited by examiner

*Primary Examiner* — Bin Shen

(57) ABSTRACT

The present invention is directed generally to dry cell culture media or feeds in pellet formats which can be reconstituted into liquid media for culturing cells in vitro. Each pellet composition may comprise the same or a different composition; for example, different vitamins, amino acids, buffers, trace salts, pH, iron chelators, etc. The invention also relates to methods of making dry cell culture media by altering ratios of different pellet compositions, or, methods of making modular dry cell culture media, or customizing media formulations for growing a cell type using pellets. According to the invention, media pellets may be easier to handle either before reconstitution, during shipping and handling; and/or during reconstitution. Media pellets may be used in any container like bags including sterile, single use bags for preparing media formulations. The invention also relates to kits and culture systems using media pellets.

19 Claims, 23 Drawing Sheets

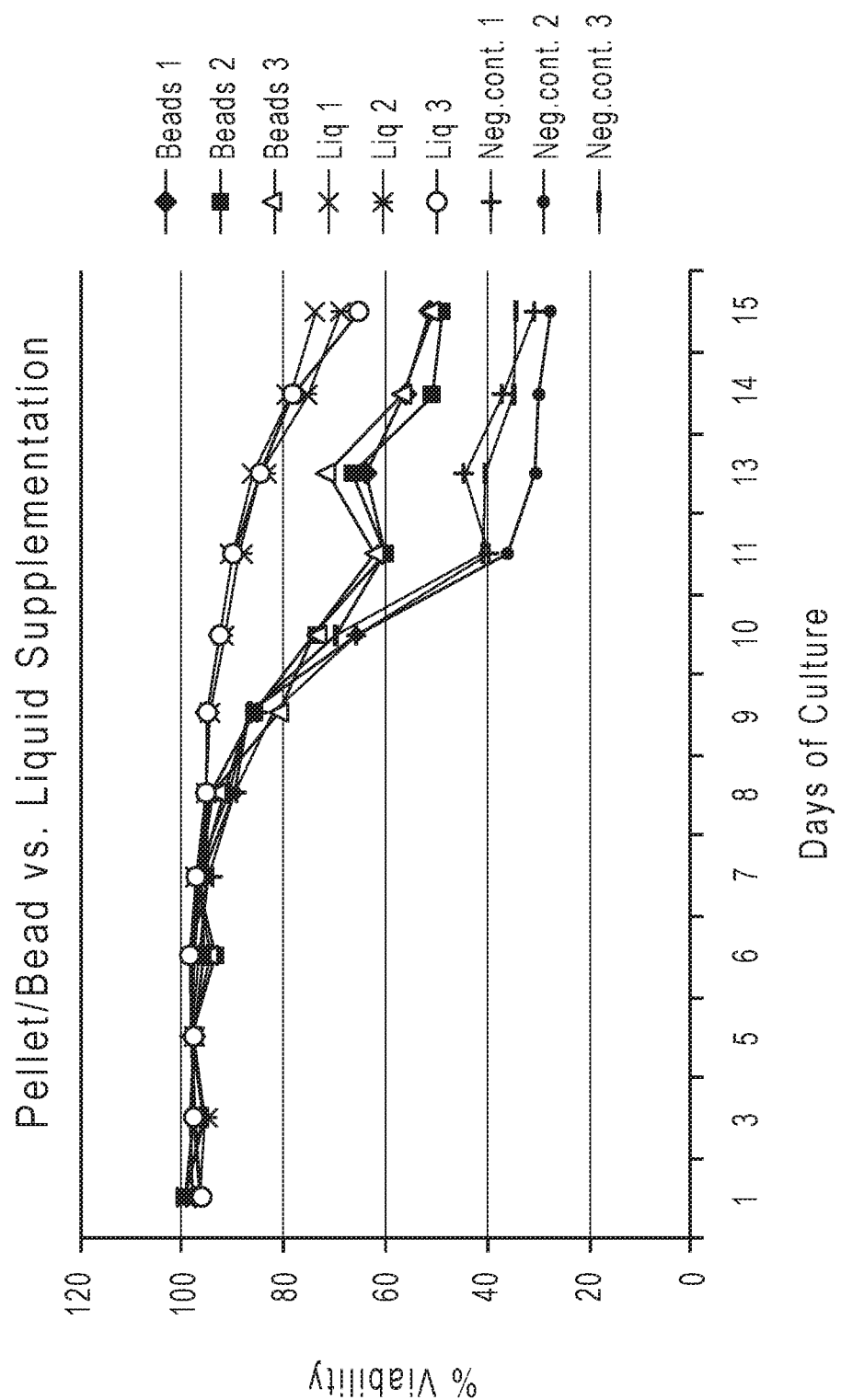

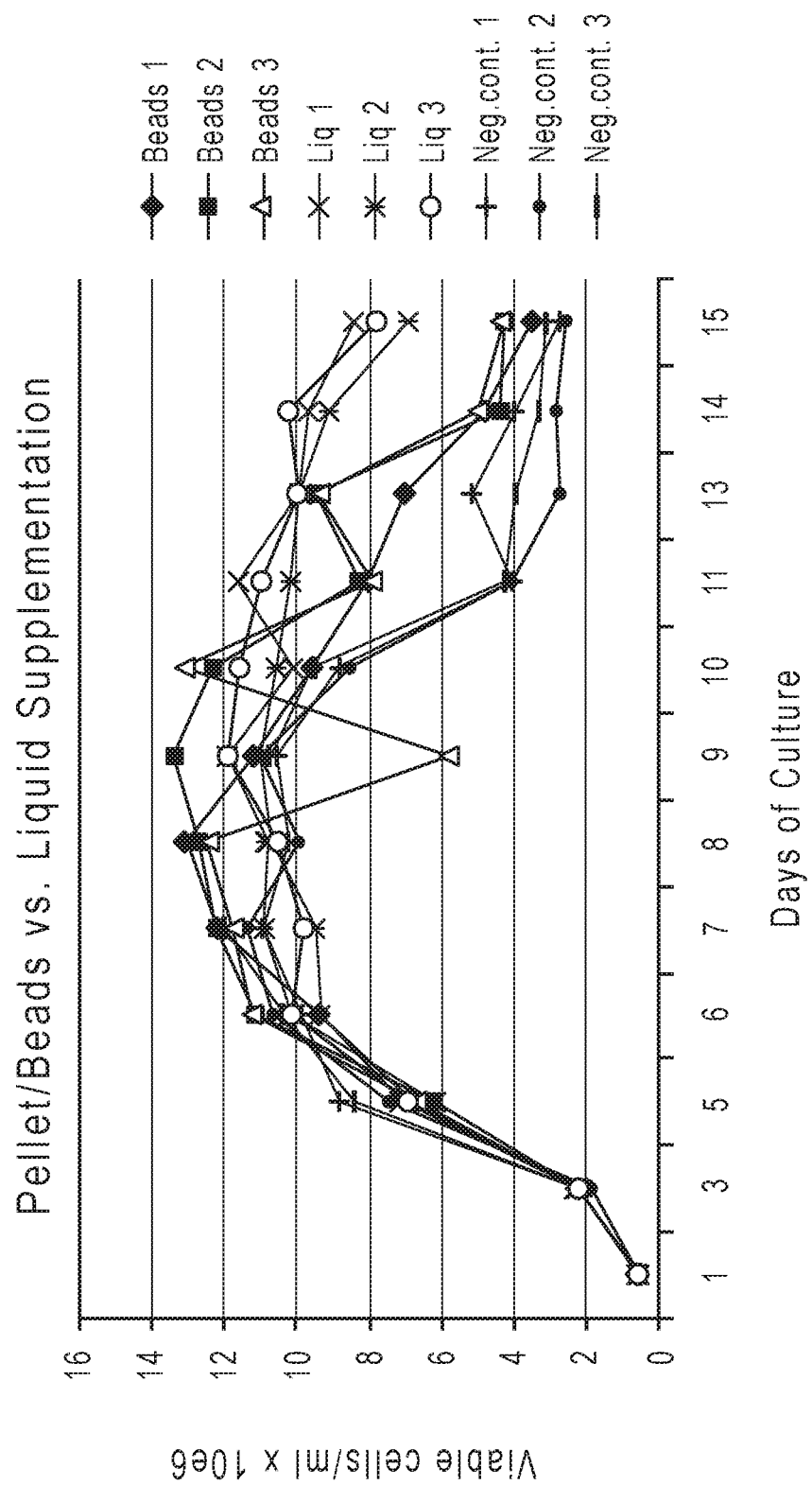

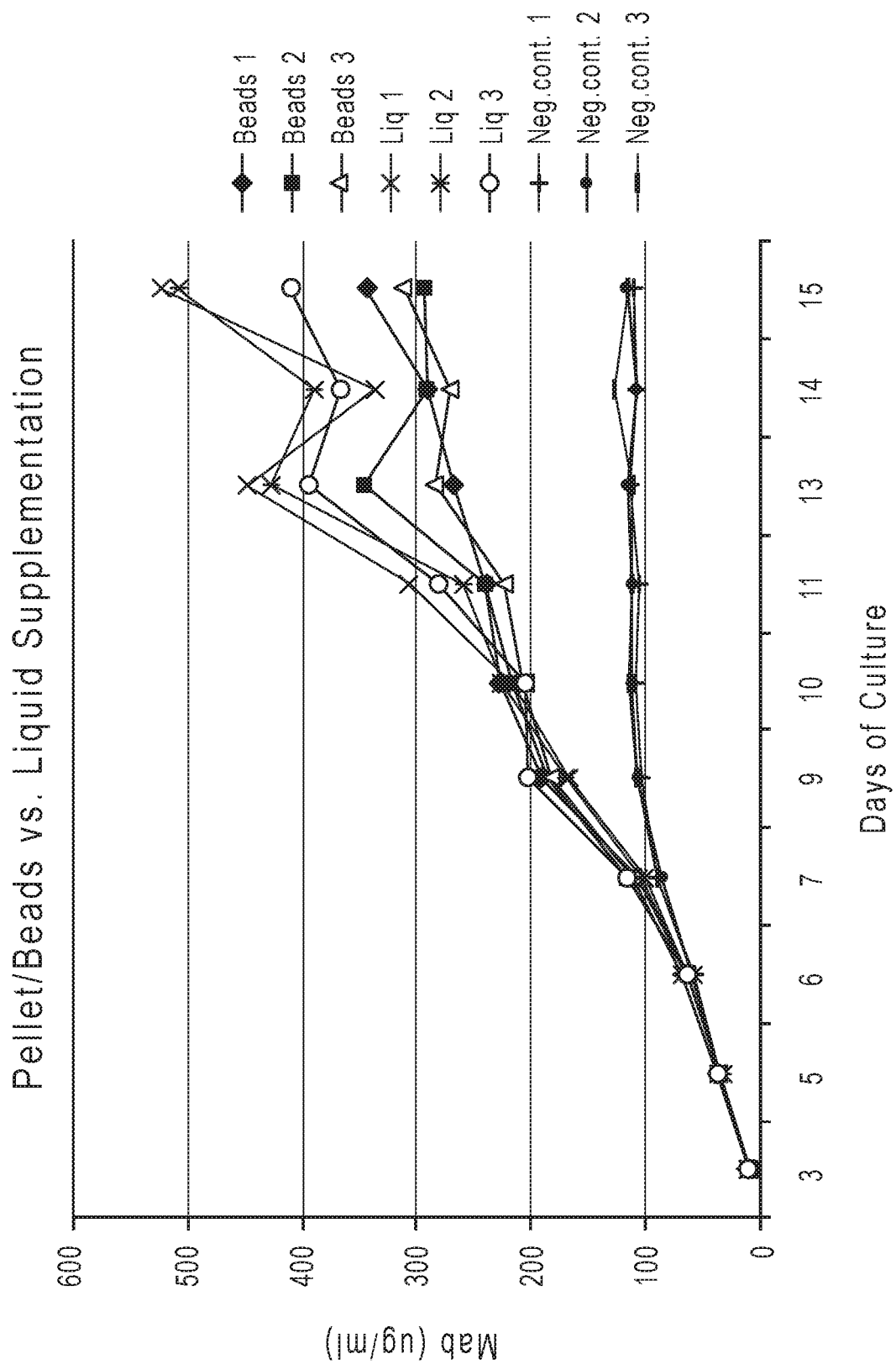

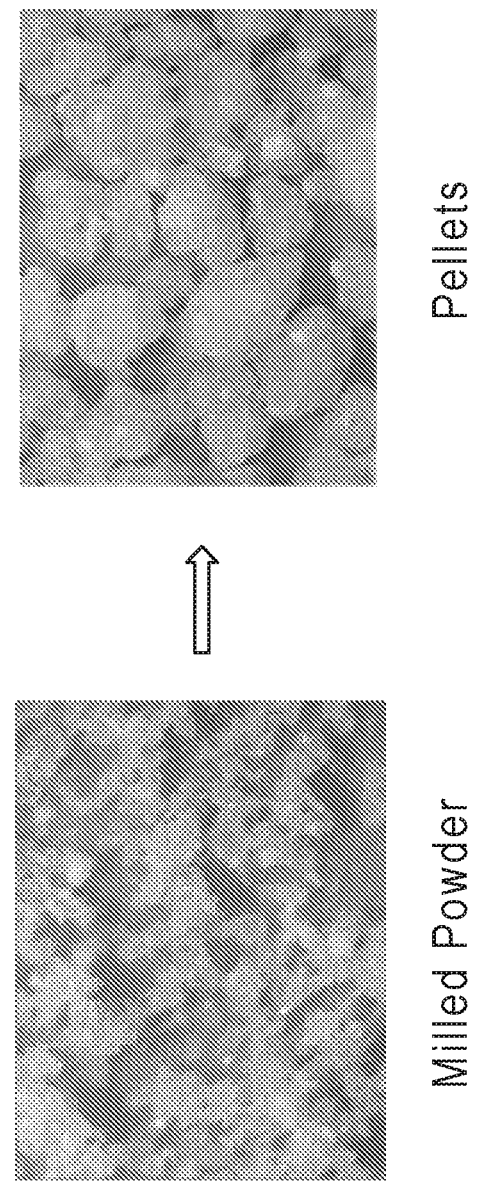
FIG. 3A: Feed 2 Pellets

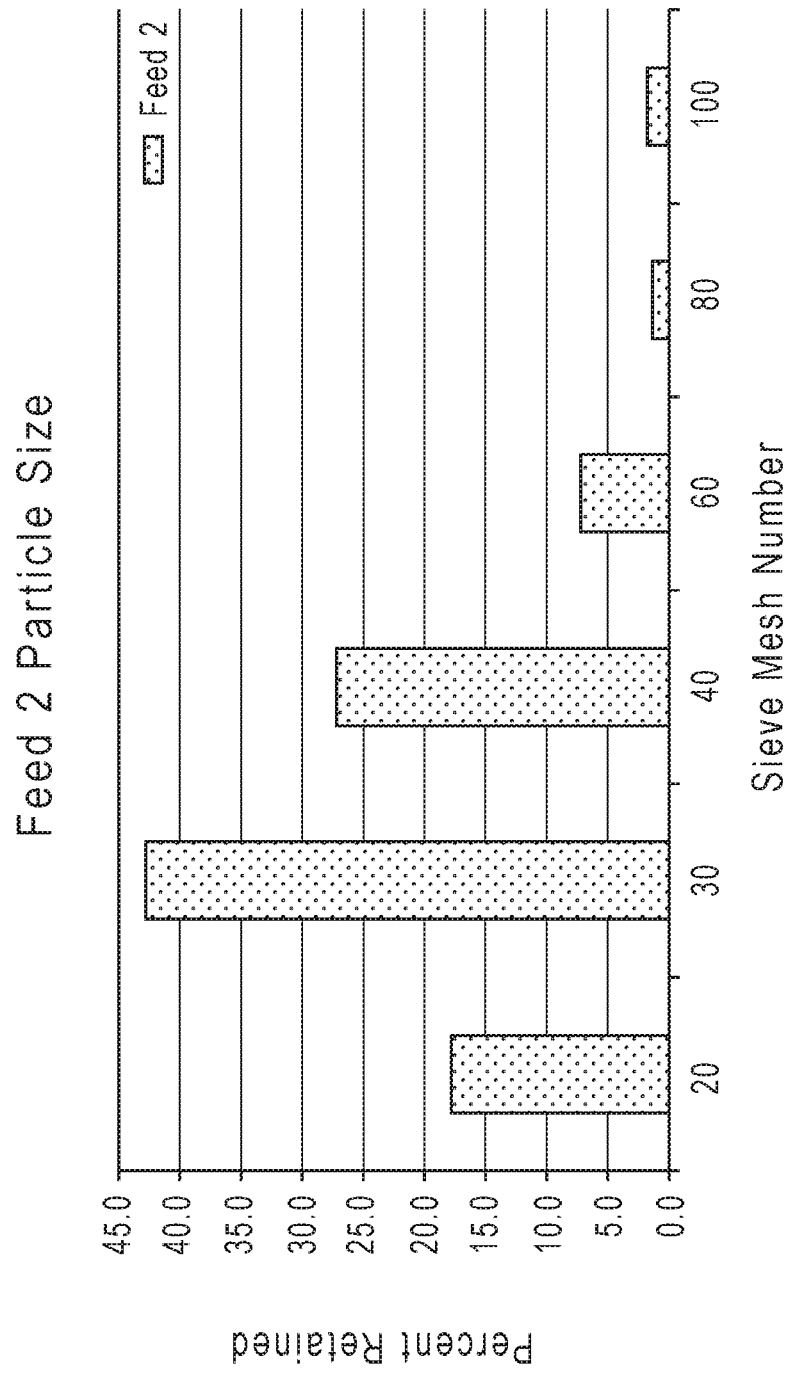
FIG. 3B: Feed 2 Pellets' Particle Size Distribution

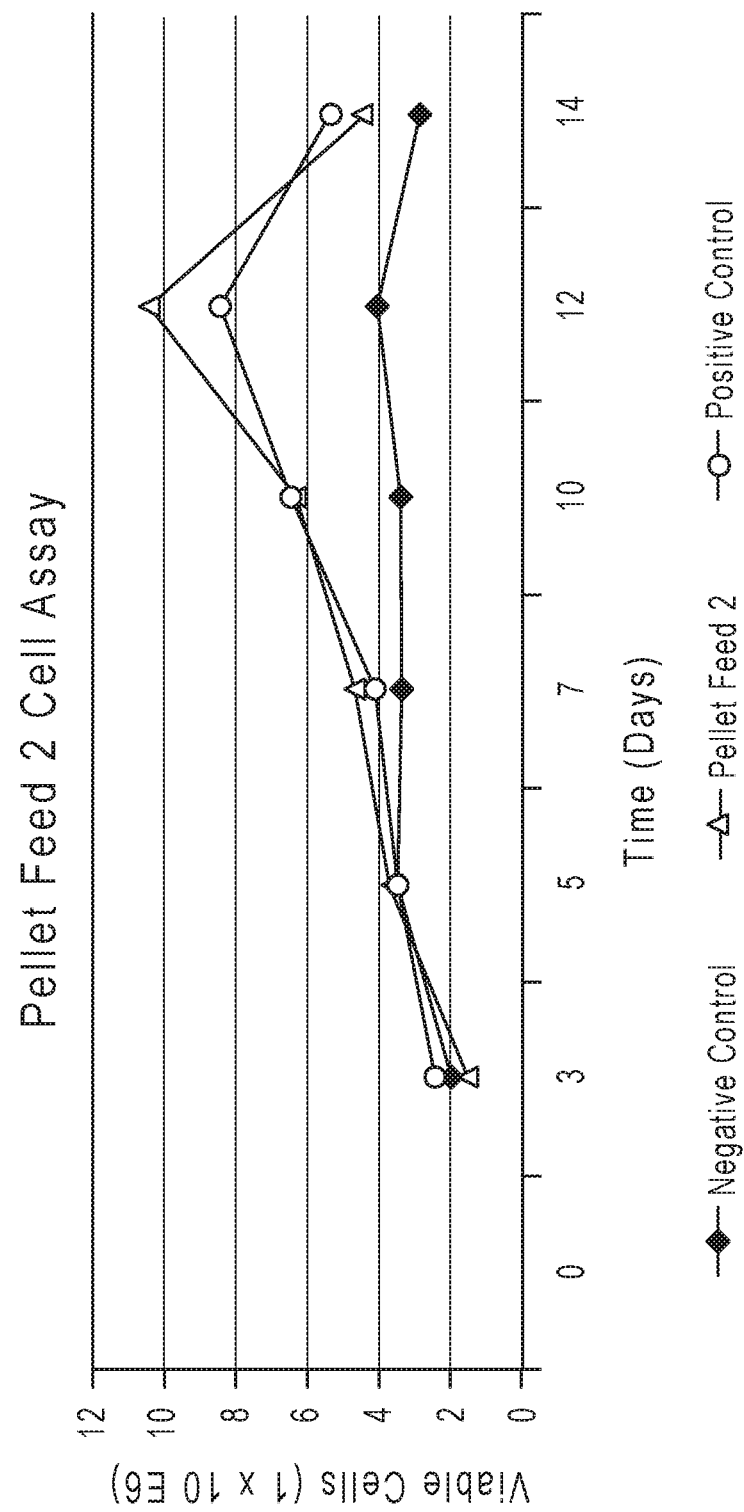

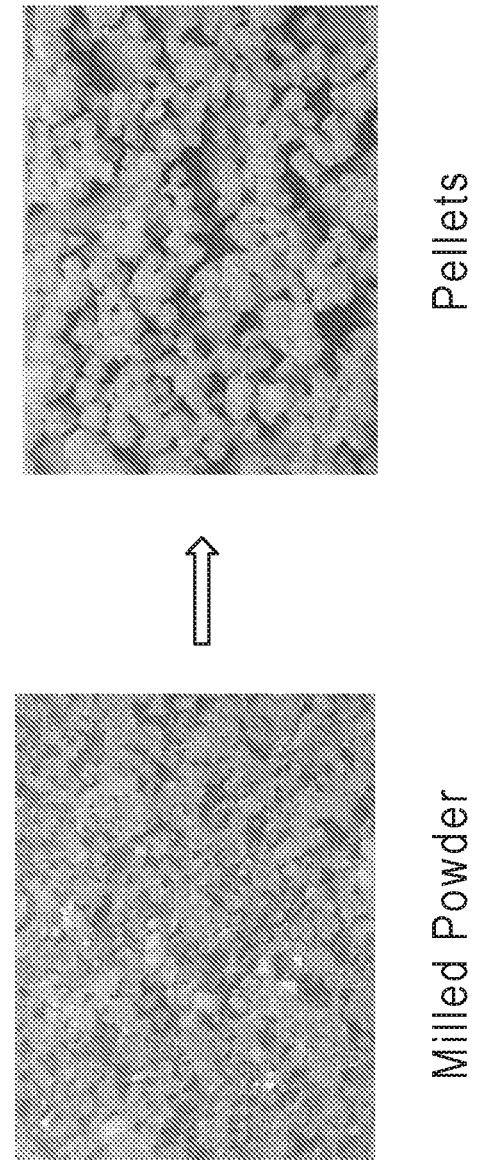
FIG. 4A: Feed 3 Pellets

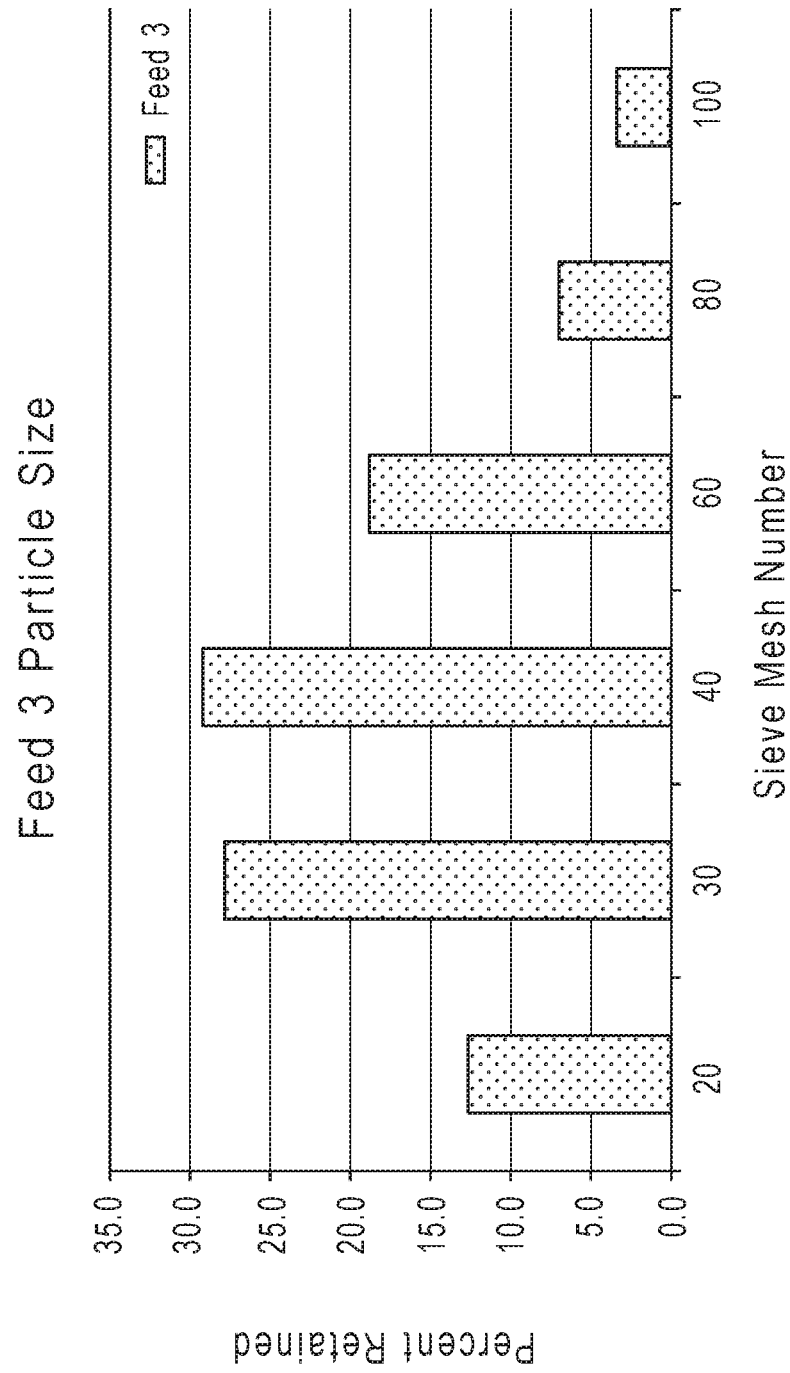
FIG. 4B: Feed 3 Pellets' Particle Size Distribution

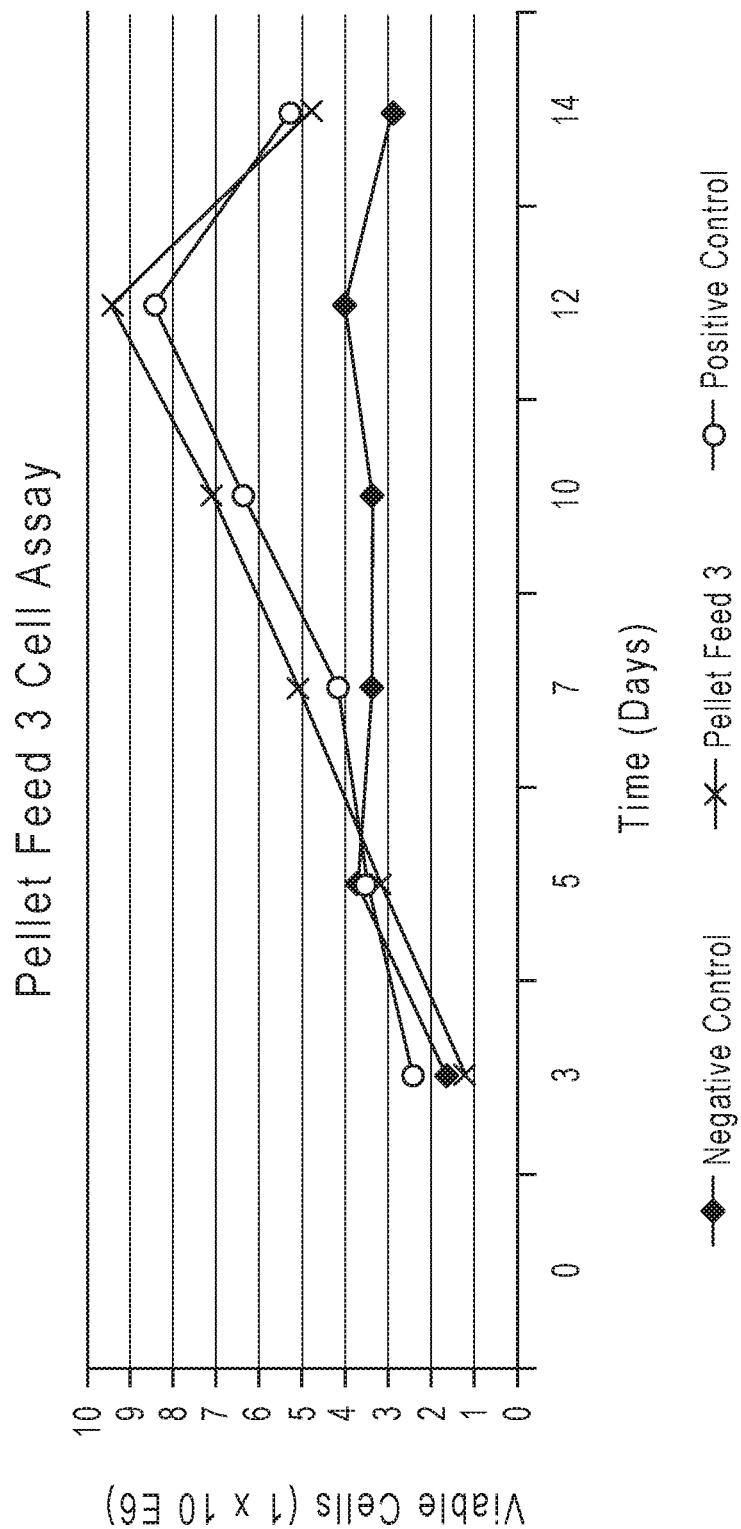

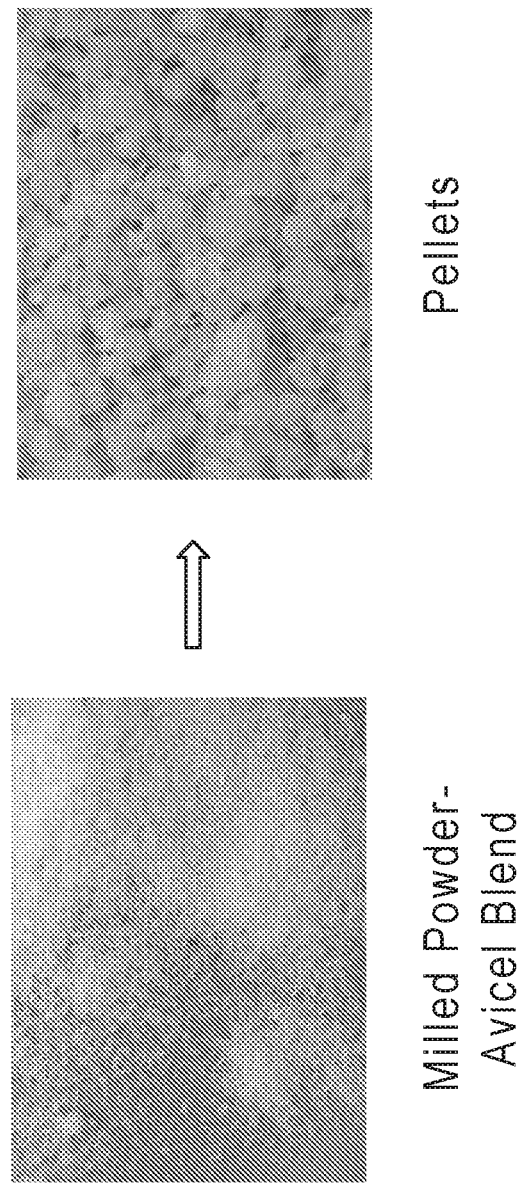
FIG. 5A: Feed 4 Pellets (with Excipient)

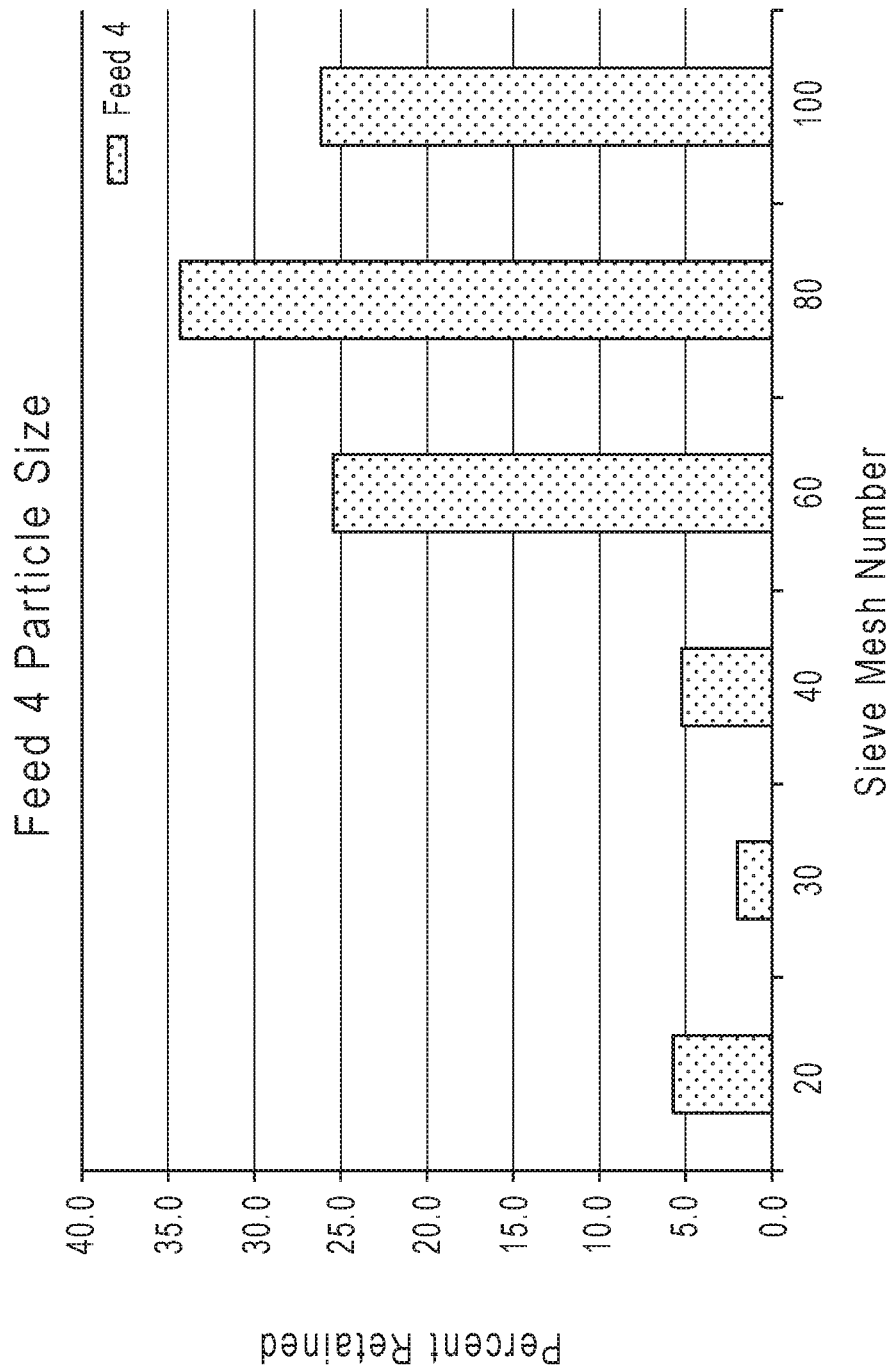

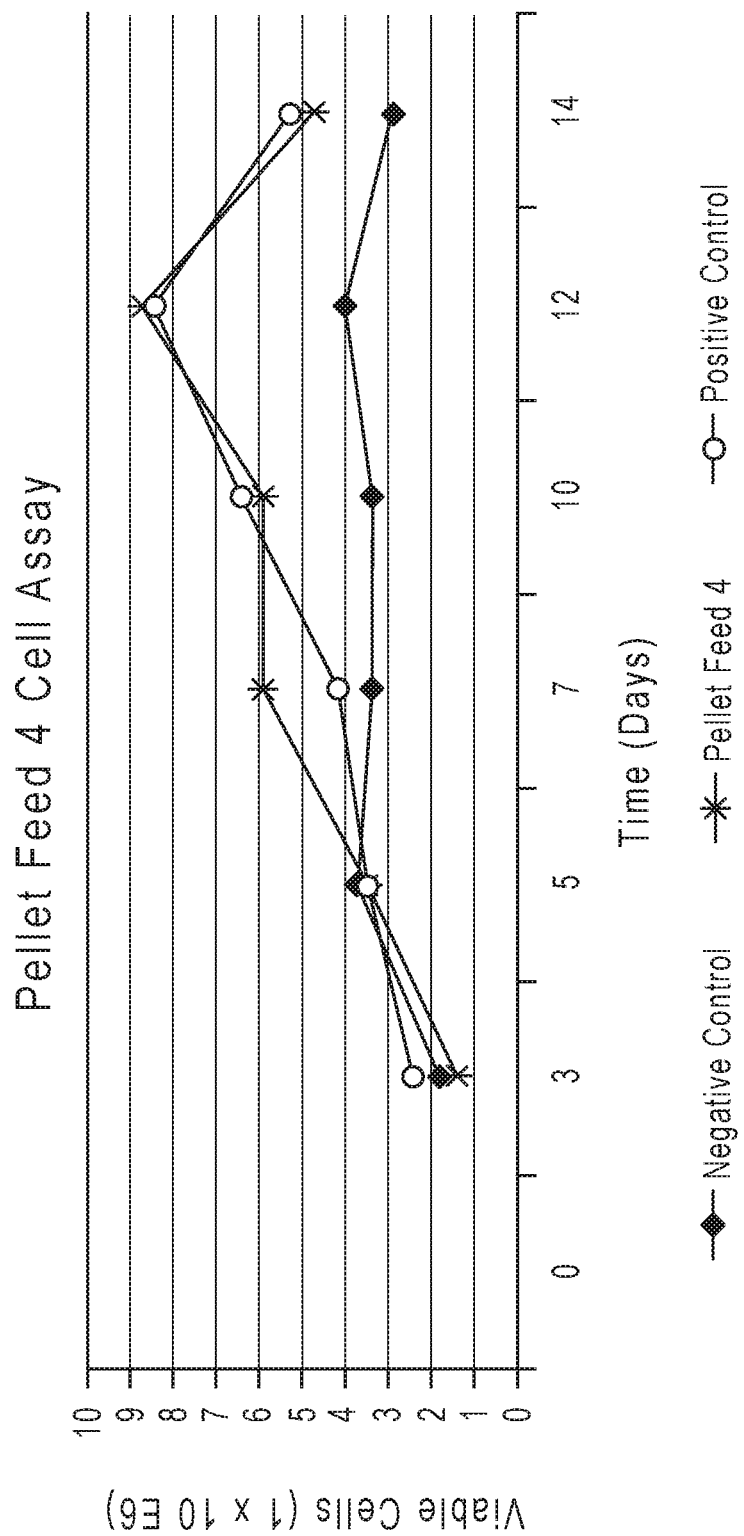

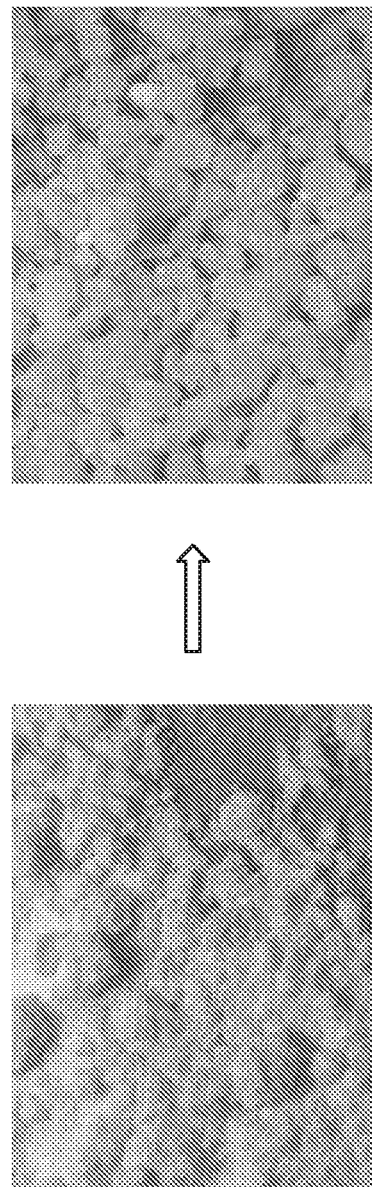
FIG. 6A: Feed 5 Pellets

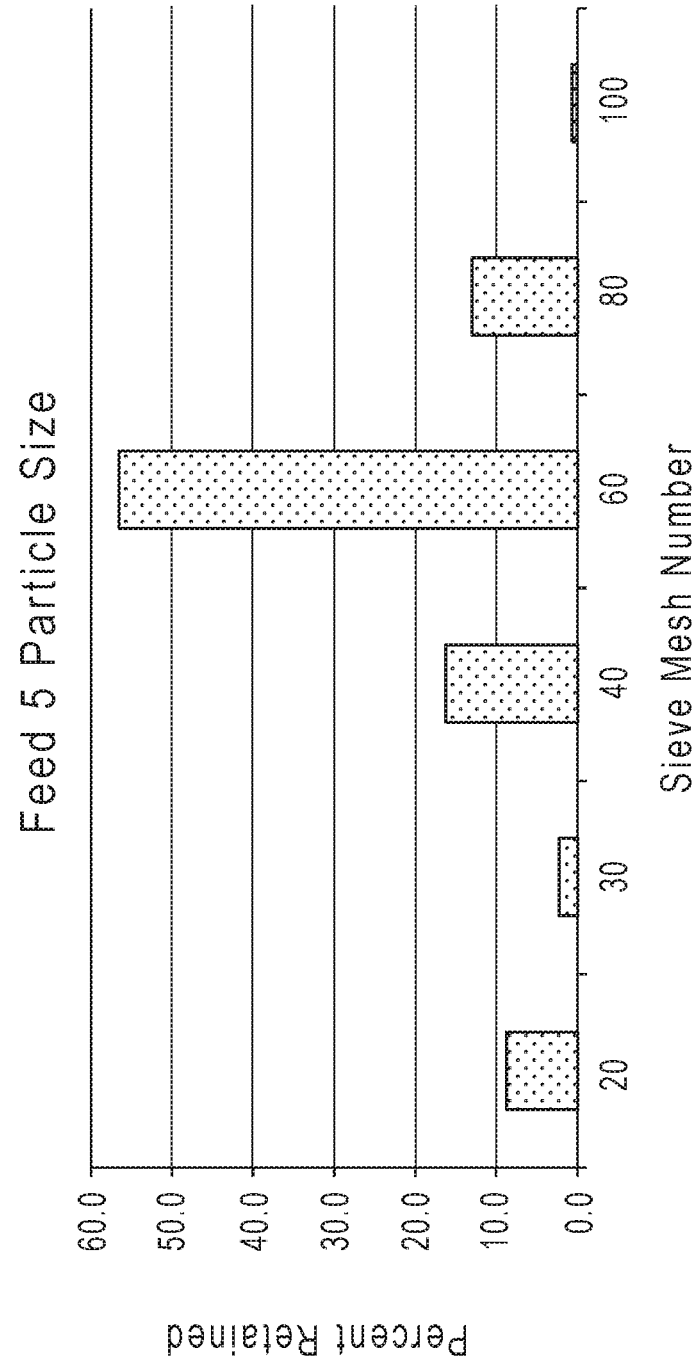

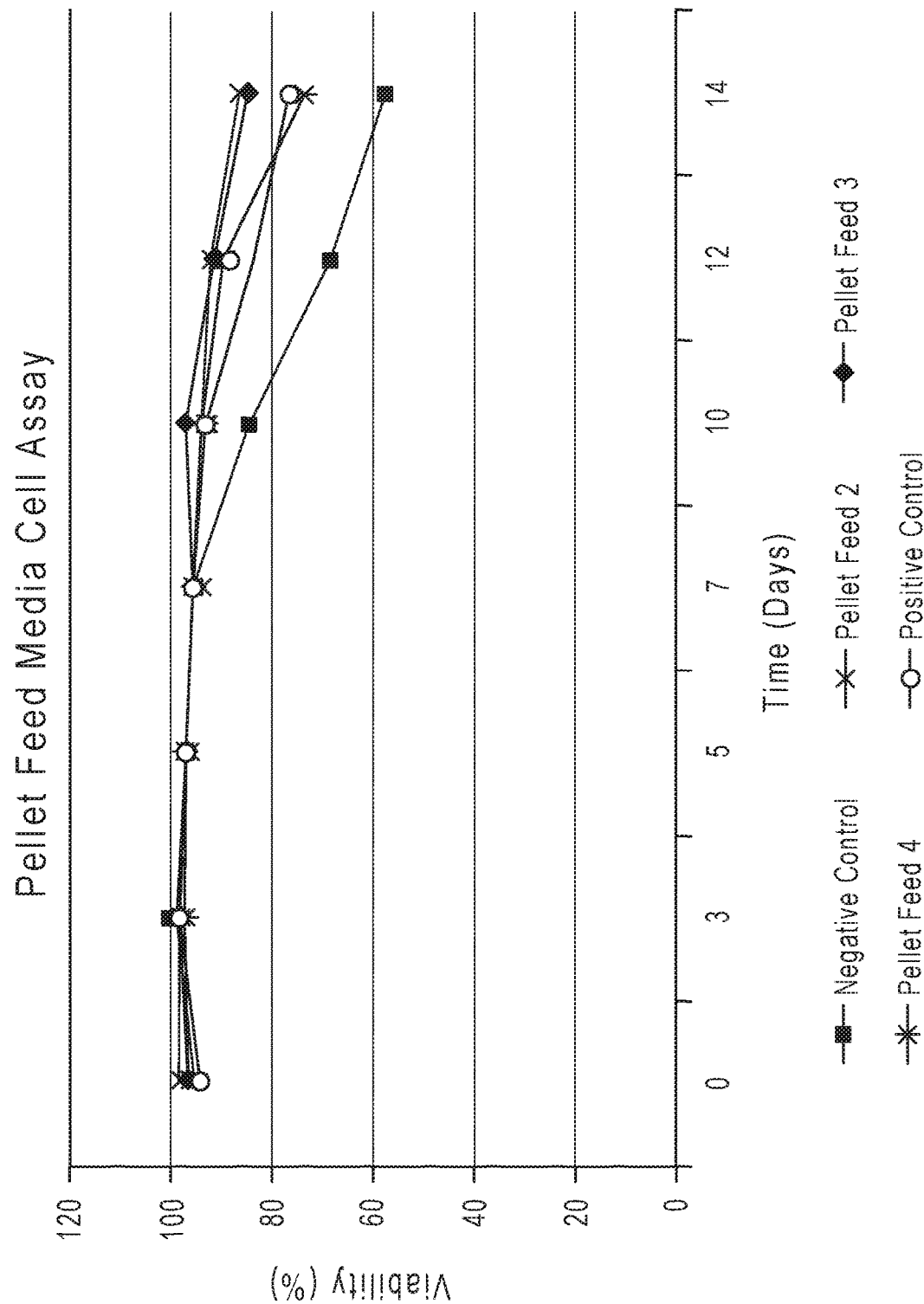

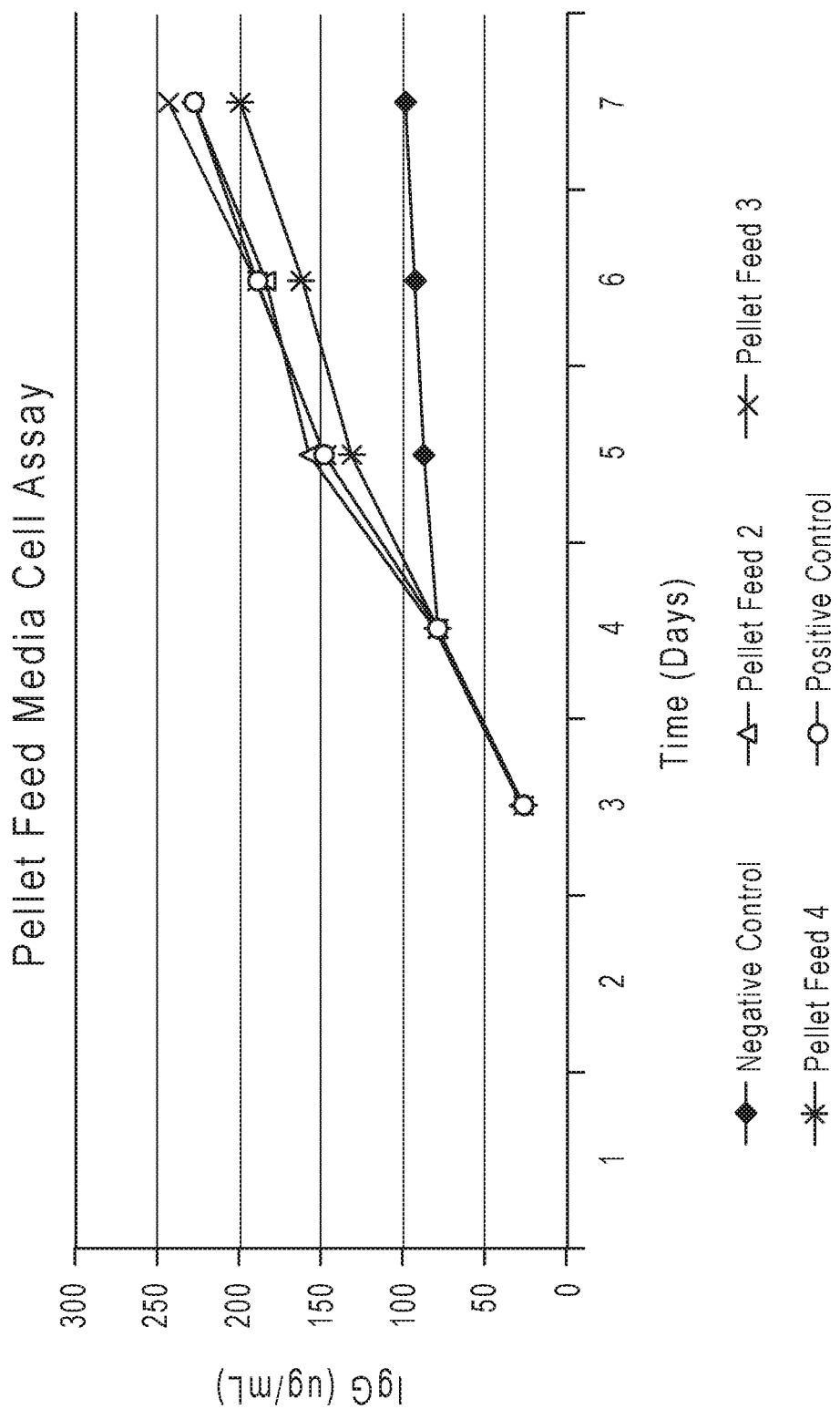
FIG. 7B: Feeds 2, 3 and 4-Protein titer

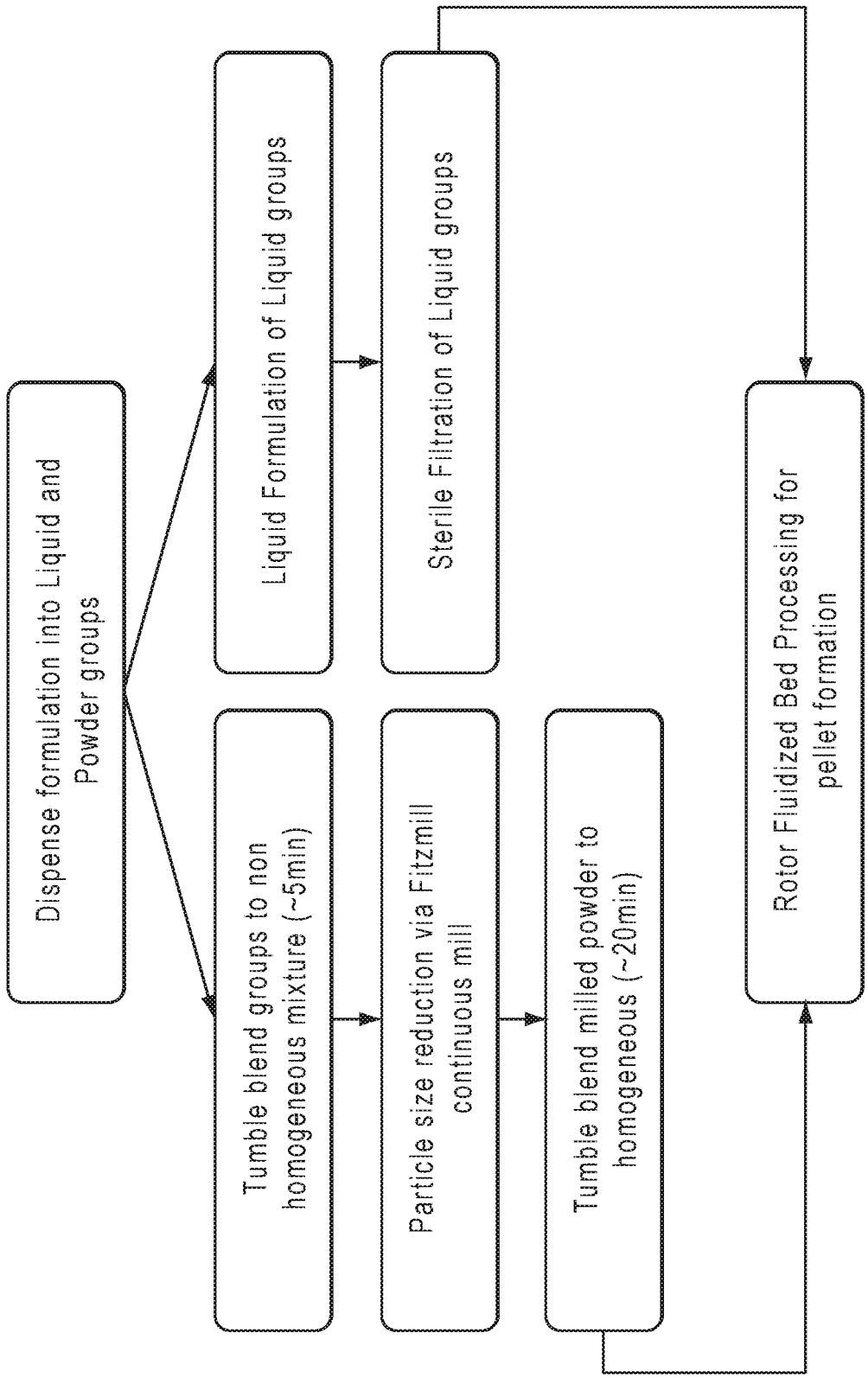
FIG. 8: Pelletizing Process

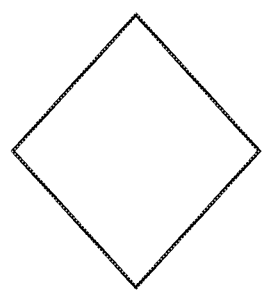 Neutral Soluble Modules
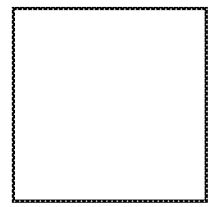 Base Soluble Modules
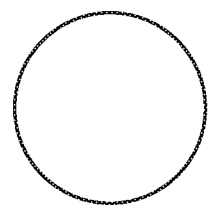 Acid Soluble Modules
FIG. 9A

PELLETS USED IN CELL CULTURE AND METHODS OF MAKING THEREOF

CROSS-REFERENCE

This application is a 371 of International Application No. PCT/US2016/67374, filed Dec. 16, 2016, which claims the benefit under 35 U.S.C. § 119(e) of U.S. Provisional Application No. 62/269,031, filed 17 Dec. 2015. The entire content of the aforementioned application is incorporated by reference herein.

FIELD OF THE INVENTION

The present invention relates to pelletized dry cell culture media, feeds, supplements, concentrates or media buffers useful in culturing cells and other such applications. The invention relates to processes for preparing such pelletized compositions and methods to tune the pellet to a desired particle size. The invention also relates to the use of such pellet preparations to produce proteins and polypeptides, and to increase cell growth and protein titers thereby.

BRIEF SUMMARY OF THE INVENTION

A first aspect of the invention is directed to a method of making a pelletized cell culture medium, the method comprising: a) subjecting a first dry powder to suspension in an upwardly moving column of a gas in a fluid bed apparatus, and to spinning in a disc rotor; b) introducing a solvent and/or a second dry powder into the fluid bed apparatus at step (a), such that the pellet is formed; and c) drying the pellet, wherein the first dry powder, the second dry powder, or the solvent comprises a binder, an excipient, or both.

In a further aspect, the first dry powder of step (a) may be pre-wetted, and optionally, no solvent may be introduced in step (b).

In some aspects, the first and second dry powders can be the same, and in other aspects, the first and second dry powders can be different.

In a particular aspect, the first dry powder may be selected from the group consisting of a basal media powder, a complete media powder, a feed, a supplement, a media or feed concentrate and an amino acid mixture that can support the cultivation of a cell in culture. In another aspect, the second dry powder may be selected from the group consisting of a basal media powder, a complete media powder, a feed, a supplement, a media or feed concentrate and an amino acid mixture that can support the cultivation of a cell in culture.

A second aspect of the invention provides binders or excipients or both, that are present either in the first powder, the second powder, in the solvent or in any and are used in the methods described. In another aspect the binder or the excipient may be selected from the group consisting of a sugar, a natural substance, a synthetic substance and a semisynthetic substance. In a particular aspect, the natural substance may be for example, microcrystalline cellulose.

In a particular aspect the invention provides sugars, that are present either in the first powder, the second powder, in the solvent or in any and are used in the methods described; and the sugar may be selected from the group consisting of glucose, sucrose, trehelose, a monosaccharide, a disaccharide and an oligosaccharide. In a further aspect the sugar may be glucose, and the glucose in the pellet may be at a concentration of from 0.1 to 100% of the pellet composition. In a particular embodiment, the sugar comprises D-glucose.

In one embodiment, the invention provides vitamins that are present either in the first powder, the second powder, in the solvent or in any, and are used in the methods described. In a particular embodiment, the vitamins are selected from one or more of vitamin B12, biotin, choline, folic acid, niacinamide, pyridoxine, riboflavin, thiamine, ascorbic acid, para-aminobenzoic acid (PABA), etc.

In another embodiment the invention provides salts that may be present either in the first powder, the second powder, or in the solvent and are used in the methods described. In one embodiment, the salts are selected from one or more of buffer salts, iron, zinc, calcium, copper, magnesium, manganese, ammonium, vanadium salts, etc.

In yet another embodiment, the invention provides amino acids that are present either in the first powder, the second powder, in the solvent or in any and are used in the methods described. In one embodiment, amino acids are selected from one or more of the well-known twenty amino acids, their salts or derivatives thereof. In another embodiment, the amino acids are selected one or more of glycine, alanine, arginine, aspartic acid, glutamic acid, histidine, isoleucine, methionine, phenylalanine, proline, hydroxyproline, serine, threonine, tryptophan, valine, tyrosine, cysteine and lysine.

In yet another aspect, the invention provides binders that are present either in the first powder, the second powder, in the solvent or in any and are used in the methods described. In some embodiments, binders or excipients may be used interchangeably or together throughout the specification. In one embodiment, the binders or excipients are selected from the group consisting of a sugar, a natural substance, a synthetic substance and a semisynthetic substance, microcrystalline cellulose, glucose, sucrose, trehelose, a monosaccharide, a disaccharide and an oligosaccharide, excipients and/or disintegrants. In one particular embodiment, the binders are microcrystalline cellulose and glucose. In another embodiment the percent composition of binder(s) in the pellet may be from about 0.1 to about 100%. In a particular embodiment, the % composition of binder(s) in the pellet may be from about 30 to about 60%.

A third aspect of the invention provides methods of making the pellet of various sizes; in some instances, the pellet has a size of about 0.05 mm to 7 mm. In a particular aspect the invention provides pellets having a size of about 0.05 mm to about 0.5 mm, or about 0.05 mm to about 1 mm, or about 0.05 mm to about 2 mm, or about 0.05 mm to about 3 mm, or about 0.05 mm to about 4 mm, or about 0.05 mm to about 5 mm, or about 0.05 mm to about 6 mm, or about 0.05 mm to about 0.1 mm, or about 0.05 mm to about 0.2 mm, or about 0.05 mm to about 0.3 mm, or about 0.05 mm to about 0.4 mm, or about 0.1 mm to about 1 mm, or about 0.1 mm to about 2 mm, or about 0.1 mm to about 3 mm, or about 0.1 mm to about 4 mm, or about 0.1 mm to about 5 mm, or about 0.1 mm to about 6 mm, or about 0.5 mm to about 1 mm, or about 0.5 mm to about 2 mm, or about 0.5 mm to about 3 mm, or about 0.5 mm to about 4 mm, or about 0.5 mm to about 5 mm, or about 0.5 mm to about 6 mm, or about 0.5 mm to about 7 mm, or about 1 mm to about 2 mm, or about 1 mm to about 3 mm, or about 1 mm to about 4 mm, or about 1 mm to about 5 mm, or about 1 mm to about 6 mm, or about 1 mm to about 7 mm. In a particular embodiment, the invention provides pellet preparations mostly having a size pellet size may be larger than about 0.1 mm, or larger than about 0.2 mm, or larger than about 0.3 mm, or larger than about 0.4 mm, or larger than about 0.5 mm, or larger than about 0.6 mm, or larger than about 0.7 mm, or larger than about 0.8 mm, or larger than about 0.9 mm, or larger than about 1 mm, or larger than about 2 mm.

In other aspects of making the pellets of the invention, the methods may be directed to the use of disc rotors in the process chamber that spin at variable speeds.

In other aspects, the solvent introduced into step (a) when subjecting a first dry powder to suspension in an upwardly moving column of a gas in a fluid bed apparatus, and to spinning in a disc rotor, the solvent is introduced through a tangential spray, a top spray, or a bottom spray. In a further aspect, the rate of the solvent introduced into step (a) may be between about 1 gm/min up to about 30 gm/min. In a particular aspect, rate of the solvent introduced into step (a) may be about 5 gm/min.

A fifth aspect of the invention provides methods of making the pellets, wherein the temperature of the inlet gas may be at about 20° C. to 30° C. In a particular aspect, the temperature of the inlet gas may be at about 25° C. In a further aspect, the pellet temperature may be maintained at about 20° C. to 30° C. In yet another aspect, the temperature for drying the pellet may be about 50° C. to 60° C. And in an aspect, the pellet may be dried to a moisture content of about 0.5% to 3%.

A sixth aspect of the invention provides methods of making a pelletized base powder modules, the method comprising: a) subjecting a first dry powder to suspension in an upwardly moving column of a gas in a fluid bed apparatus, and to spinning in a disc rotor; b) introducing a solvent and optionally, a second dry powder into the fluid bed apparatus at step (a), such that the pellet of the base powder module may be formed; and c) drying the pellet, wherein the first dry powder, the second dry powder, or the solvent comprises a binder, an excipient, or both.

A further aspect of the invention provides method of making a pelletized base powder module wherein the module may be selected from the group consisting of one or more water soluble vitamins, one or more acid soluble vitamins, one or more neutral soluble vitamins, one or more acid soluble amino acids, one or more based soluble amino acids, one or more neutral water soluble amino acids, one or more water soluble, inorganic salts, one or more inorganic, acid soluble salts, one or more sugars, one or more acid soluble, trace elements, one or more alcohol soluble polyamines, one or more alcohol soluble lipids, and one or more buffer salt. In one aspect of the invention, the water soluble or acid or base or neutral soluble vitamin module, the water soluble or acid or base or neutral soluble amino acid module, or the water soluble or acid or base or neutral soluble salts module comprises at least one water insoluble excipient or water insoluble binder or both.

In another aspect, the pelletized base powder module may be selected from the group consisting of one or more water soluble groups, one or more base soluble groups, one or more acid soluble groups, one or more acid soluble reactive groups, one or more alcohol soluble groups, one or more alcohol soluble reactive groups and one or more pH modifier groups. In a particular aspect, the water soluble group may be selected from the group consisting of vitamins, bulk inorganic salts and sugars.

A seventh aspect of the invention provides pellets obtained by or obtainable by any one of the methods described above.

In an eighth aspect, the invention may be directed to a pelletized cell culture medium, feed, supplement or additive comprising one or more amino acids, one or more binders or excipients and one or more trace components.

In one embodiment, the pelletized cell culture medium, feed, supplement or additive further comprises vitamins. In a particular embodiment, the vitamins are selected from one or more of vitamin B12, biotin, choline, folic acid, niacinamide, pyridoxine, riboflavin, thiamine, ascorbic acid, para-aminobenzoic acid (PABA), etc.

In another aspect, the pelletized cell culture medium, feed, supplement or additive further comprises salts. In one embodiment, the salts are selected from one or more of buffer salts, iron, zinc, calcium, copper, magnesium, manganese, ammonium, vanadium salts, etc.

In yet another aspect, the pelletized cell culture medium, feed, supplement or additive comprises amino acids selected from one or more of the well-known twenty amino acids, their salts or derivatives thereof. In one embodiment, the amino acids are selected one or more of glycine, alanine, arginine, aspartic acid, glutamic acid, histidine, isoleucine, methionine, phenylalanine, proline, hydroxyproline, serine, threonine, tryptophan, valine, tyrosine, cysteine and lysine.

In an ninth aspect, the invention may be directed to a pelletized cell culture medium, feed, supplement or additive of claim comprising binders or excipients, which may be used interchangeably or together throughout the specification. In one embodiment, the binders or excipients are selected from the group consisting of a sugar, a natural substance, a synthetic substance and a semisynthetic substance, microcrystalline cellulose, glucose, sucrose, trehelose, a monosaccharide, a disaccharide and an oligosaccharide, excipients and/or disintegrants. In one particular embodiment, the binders are microcrystalline cellulose and glucose. In another embodiment the % composition of binder(s) in the pellet may be from about 0.1 to about 100%. In a particular embodiment, the % composition of binder(s) in the pellet may be from about 30 to about 60%.

In an tenth aspect, the composition described throughout the invention may be directed to a pelletized cell culture medium, feed, supplement or additive of claim comprising one or more of 25-40% amino acids, 20-65% binders, 1-5% vitamins, 2-10% salts, 0.01-0.05% trace components. In a particular embodiment, the pellet compositions comprises one or more of 31-32% amino acids, 59-60% binders, 25% vitamins, 6-7% salts, 0.01-0.05% trace components. In a preferred composition the binder is D-glucose.

In an eleventh aspect, the invention provides methods of producing a nutritive medium pellet, a nutritive medium supplement pellet, a nutritive medium subgroup pellet or a buffer pellet, the method comprising: agglomerating a dry powder medium, supplement, medium subgroup, or medium buffer with a solvent and forming a pellet using a rotating disk in a fluid bed, wherein the pellet comprises a binder or excipient.

Another aspect of the invention provides methods of producing a nutritive medium pellet, a nutritive medium supplement pellet, a nutritive medium subgroup pellet or a buffer pellet, wherein the binder or excipient may be sprayed in through the solvent, or may be blended into the dry powder before pelletization. In a particular embodiment, the binder may be a sugar, and in a preferred embodiment, the sugar comprises D-glucose. The percent of binder, for e.g. glucose can be varied to achieve differential pellet size, or variable bulk density, or variable angle of repose, or variable stickiness or dryness. For example, in some embodiments, the amount could be varied from, 0-60%, or 10-16%, or 20-60%, preferably 30-40%, 40-50%, 30-35%, 30-45%, 40-50%, 40-55% and so on, to achieve the desired characteristics.

In another aspect, the invention may be directed to pellets obtained by, or obtainable by any one of the methods above, in all variations described above.

In a twelfth aspect, the invention provides methods of making a pellet for culturing cells comprising: preparing a microsuspension of a dry powder medium or module; extruding the microsuspension through an extruding device to form droplets; drying the droplets to pellets. An aspect may be directed to the pellets obtained thereby.

A thirteenth aspect may be directed to use of the pellets obtained by the methods of any of the above claims for culturing a cell. In an embodiment, the cell may be selected from the group consisting of eukaryotic, prokaryotic, animal, plant, fungal, algal, insect, yeast, or wherein the cell may be used for the cultivation of a virus or a viral particle. In a particular embodiment, the cell may be an animal cell. In yet another embodiment, the cell may be a mammalian cell. In a particular embodiment, the mammalian cell may be selected from the group consisting of CHO, BHK, HEK, 293, VERO, etc.

In a fourteenth aspect, the invention provides methods of culturing a cell in a liquid reconstituted from any of the pellets obtained or obtainable by the methods described above, the method comprising: i) reconstituting the pellet in a suitable liquid or buffer; wherein said pellet may be a cell culture medium, feed, supplement or concentrate; ii) culturing the cell may be the reconstituted liquid under conditions favorable for the growth of the cell. In one embodiment, the cell may be selected from the group consisting of eukaryotic, prokaryotic, animal, plant, fungal, algal, insect, yeast, or wherein the cell may be used for the cultivation of a virus or a viral particle. In another embodiment the culturing may be done to produce increased amount of a polypeptide. In a further embodiment, the polypeptide may be a recombinant polypeptide. In another embodiment, the culturing increases product production, increasing cell growth, as compared to a culture with liquid media not made from pellets.

In a fourteenth aspect, the invention provides kits comprising: i) a first container comprising a pellet obtained by, or obtainable by the methods described above, wherein said pellet may be a cell culture medium, feed, supplement or concentrate; and ii) instructions for using the pellet. In other aspects, the kits may further comprise additional containers, each of which may comprise, cells for culturing, buffers, and other components including other media (liquid or dry power, AGT format), additives, feeds, antibiotics, etc.

In a fifteenth aspect, the invention provides systems comprising a liquid medium/feed/supplement/additive reconstituted from a pellet as described above, obtainable by any one of the methods described above, and a cell. In one embodiment, the cell may be selected from the group consisting of eukaryotic, prokaryotic, animal, plant, fungal, algal, insect, yeast, or wherein the cell may be used for the cultivation of a virus or a viral particle. In another embodiment, the reconstituted liquid medium/feed/supplement/additive from the pellet may be used to cultivate a cell that produces a recombinant polypeptide, a virus, a secreted protein, or a cell either in suspension or an attached cell.

INCORPORATION BY REFERENCE

All publications, patents, and patent applications mentioned in this specification are herein incorporated by reference to the same extent as if each individual publication, patent, or patent application was specifically and individually indicated to be incorporated by reference. In case of conflict, the specification herein, including definitions, will control. Citation or identification of any reference in this application shall not be construed as an admission that such reference is available as prior art to the present invention.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized. The skilled artisan will understand that the drawings described here are for illustrative purposes only, and are not intended to limit the scope of the present teachings in any way.

FIG. 2A: Comparing cell viability assays of manually prepared Pellet Feed 1 supplement versus liquid supplement. Viability of manually prepared Pellet Feed 1 (the test sample) are shown in curves bead 1, 2, 3; Viability of liquid (the positive control) are shown in liq 1, 2, 3; Viability of un-supplemented (negative control) is shown in Neg. cont. 1, 2, 3. Cell culture supplemented with Pellet Feed 1 (done in triplicates: 1, 2, 3) showed better % viability compared to cell culture supplemented with liquid (triplicates: 1, 2, 3), especially from day 8 to 16.

FIG. 2B: Comparing cell growth assays of manually prepared Pellet Feed 1 supplement versus liquid supplement. Cell culture supplemented with Pellet Feed 1 (triplicates: 1, 2, 3) showed comparable cell growth over a period of 15 days in culture as compared to cell culture supplemented with liquid (triplicates: 1, 2, 3).

FIG. 2C: Comparing cell performance or protein titer assays of manually prepared Pellet Feed 1 supplement versus liquid supplement for antibody production. Protein titers (cell performance) of manual pellets are shown in curves bead 1, 2, 3; Protein titers of liquid (the positive control) is shown in Liq. (triplicates: 1, 2, 3); Protein titers of un-supplemented (negative control) are shown in Neg. cont. (triplicates: 1, 2, 3). Cell culture supplemented with bead/pellet 1, 2, 3 showed IgG production ~325 µg/ml (production) slightly lower than IgG produced at ~425 µg/ml with the positive liquid control EFB (triplicates: 1, 2, 3) over a period of 15 days in culture. Un-supplemented negative control showed much lower IgG production (~100 µg/ml) compared to cell culture supplemented with Feed 1 beads (test).

FIG. 3A: Microscope enlarged image of an automated pellet preparation or bead from milled powder (starting material) to Pellet Feed 2, prepared using rotor disc technology, also sometimes referred to as Feed 2 in the figures/application. The detailed method of preparation is described in the Examples.

FIG. 3B: Particle size estimation of Pellet Feed 2 prepared by rotor disc technology.

FIG. 3C: Comparing cell growth assays of automated Pellet Feed 2 versus liquid supplement. Cell culture supplemented with beads/pellet showed comparable cell growth over a period of 15 days in culture as compared to cell culture supplemented with liquid. Pellet Feed 2 showed viable cell counts ~10×10 $e^6$ cells/ml (growth) slightly higher than cell culture supplemented with Positive Control Feed (~8×10 $e^6$).

FIG. 4A: Microscope enlarged image of an automated pellet preparation or bead from milled powder (starting material) to Pellet Feed 3, prepared using rotor disc technology, sometimes referred to as Feed 3 in the figures/application. The detailed method of preparation is described in the Examples.

FIG. 4B: Particle size estimation of Pellet Feed 3 prepared by rotor disc technology.

FIG. 4C: Comparing cell growth assays of automated Pellet Feed 3 versus liquid supplement. Cell culture supplemented with Pellet Feed 3 showed comparable cell growth to positive control over a period of 14 days in culture, especially as compared to negative control (day 7 onwards). Pellet Feed 3 showed viable cell counts ~9×10 $e^6$ cells/ml (growth) slightly higher than cell culture supplemented with Positive Control Feed (~8×10 $e^6$).

FIG. 5A: Microscope enlarged image of an automated pellet preparation or bead from milled powder (starting material) to Pellet Feed 4, prepared using rotor disc technology, and where the starting dry base powder comprised a cellulose binder. It is sometimes referred to as Feed 4 in the figures/application. The detailed method of preparation is described in the Examples.

FIG. 5B: Particle size estimation of Pellet Feed 4 prepared by rotor disc technology, where the starting dry base powder comprised a cellulose binder. Graph of Pellet Feed 4 shows the result when the starting composition is chemically changed (to reduce water solubility) with cellulose. Pellet particle size was smaller compared to Feeds 2 & 3.

FIG. 5C: Comparing cell growth assays of automated Pellet Feed 4 versus liquid supplement. Cell culture supplemented with Pellet Feed 4 showed comparable cell growth to positive control over a period of 14 days in culture, especially as compared to negative control (day 7 onwards).

FIG. 6A: Microscope enlarged image of an automated pellet preparation or bead from milled powder (starting material) to Pellet Feed 5, prepared using rotor disc technology, and where the starting dry base powder was first micronized into smaller particle sizes before its use in the pelletization process. It is sometimes referred to as Feed 5 in the figures/application. The detailed method of preparation is described in the Examples.

FIG. 6B: Particle size estimation of Pellet Feed 5 prepared by rotor disc technology, where the starting dry base powder was first micronized into smaller particle sizes. Graph shows the result when the starting composition is physically changed (reduced particle size). Particle size was more homogeneous.

FIG. 7A: Biological Evaluation of Pellet Feeds. Viability assays were performed for Pellet Feeds 2, 3 and 4 and compared to positive (with liquid feed supplementation) or negative controls (no liquid or pellet supplementation). As seen from the graph, Feeds 2, 3 and 4 compared well, like the positive control and better than the negative control, especially after day 6. Cell viability assays for Pellet Feed 5 yielded similar results like Feeds 2, 3 and 4 (data not shown).

FIG. 7B: Biological Evaluation of Pellet Feeds. Cell performance (antibody production) assays were performed for Pellet Feeds 2, 3 and 4 and compared to positive (with liquid feed supplementation) or negative controls (no liquid or pellet supplementation). As seen from the graph, Feeds 2, 3 and 4 compared well, like the positive control and better than the negative control, especially after day 4. Cell culture supplemented with Pellet Feed 2 (~229 µg/ml) showed IgG production comparable with IgG produced ~228 µg/ml (at day 14) with the Positive Control Feed; cell culture supplemented with Pellet Feed 3 (~243 µg/ml) showed IgG production slightly higher than the Positive Control Feed; and cell culture supplemented with Pellet Feed 4 (~200 µg/ml) showed IgG production slightly lower than the Positive Control Feed. The un-supplemented cell culture assay (negative control) showed much lower IgG (~100 µg/ml) when compared with cell culture supplemented with any Pellet Feed 2, 3 or 4. Cell performance (antibody production) assays for Pellet Feed 5 yielded similar results like Feeds 2, 3 and 4, (data not shown).

FIG. 8: The pellet making process: Pelletization occurs through the wetting of dry powder in a fluidized rotor. In an exemplary pellet process, medium components are weighed into separate groupings in order to limit pre-processing interactions. Groupings to be used in the dry powder are segregated from those components which will be sprayed into the fluidized powder. Either the dry powder, or the spray solution, or both will contain a binder. Sprayed solutions are formulated and the dry powder components are milled and blended to homogeneity. Here, directly pelletizing from powder used rotor technology.

FIGS. 9A and 9B: Exemplary components or groupings for making modular media, feeds or supplement pellets. Categories are made based on their properties like solubility, or their tendencies to react adversely with other components. Generally, adverse reactants are kept separate until the final stage, when they are added together, carefully to prevent precipitation, or adduct formation (which would render the product useless) when the pellets are finally reconstituted with liquid. Exemplary categories are neutral soluble components, base soluble components, acid soluble components.

DETAILED DESCRIPTION OF THE INVENTION

Figure 1A:
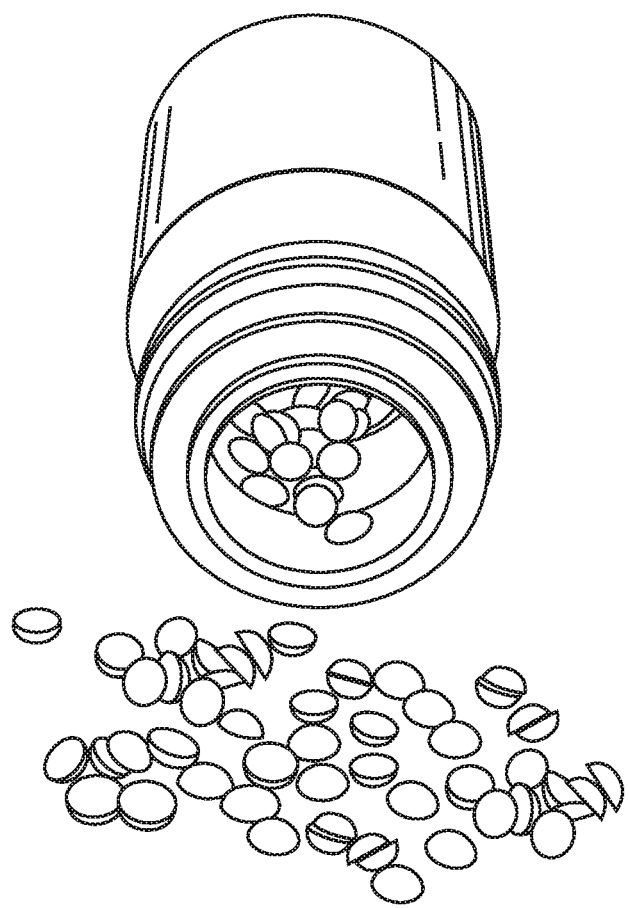
FIG. 1A: A manually prepared pellet or bead, Pellet Feed 1 is shown here. The detailed method of preparation is described in Example 1. 1B: Visual size estimation of the Pellet Feed 1. 1C: Visual size comparison of the Pellet or bead Feed 1.

The invention relates to methods of producing dry powder media. Dry powder media when mentioned in this disclosure may refer to dry powder media (basal media or complete media), dry concentrated cell culture media, dry powder feeds or supplements, dry powder concentrated feeds or supplements, dry buffer powders, which may be used in combination, or in part, or by itself (when it is a complete medium) in culturing a cell. Generally, culturing refers to culturing a cell in vitro. A method of pelletized media or feeds according to the present invention will be described hereinafter.

A typical work flow in a cell culture bio therapeutic production requires open air dispensing, reconstitution of dry powder medium, additional formulation steps followed by pH/osmolarity adjustments, filtration and transfer to a bioreactor. This multi-step process has the potential to introduce risk through erroneous formulation or through contamination by unwanted adventitious agents (for e.g., bacteria, viruses, mycoplasma, etc).

A desirable solution to the above problem would be to provide a complete cell culture medium or a feed for supplementation in a dry format, such that the medium or feed can be hydrated in a 'closed system' before being added to the bioreactor. The present invention relates to fluid bed pelletizing basal or complete cell culture media powders, feed powders, supplement powders, buffer powders, vitamin powders, additive powders, or the like, for the preparation of pellet or micro-pellet formats that can be used with ease in such 'closed systems'. The application of powdered cell culture media powder as "micro pellets" with compact size, good flow properties may be much easier to reconstitute into liquid for use in biopharmaceutical production than a dry powder with fine powder particles that flies around, causing loss of materials.

The fluid bed pelletizing process may be adapted from the pharmaceutical industry; pharmaceutical compositions comprise a couple to several ingredients in a composition. For example, pharmaceutical compositions may comprise one to a maximum of ten components. On the other hand, cell culture media powders, feed powders, supplement powders used for the cultivation of cells, particularly animal cells, more particularly mammalian cells, and even more particularly, recombinant cells for production of recombinant proteins and vaccines, are highly complex in that they generally comprise 80 to 100 individual components, each required in precise amounts. Some of the media components, like salts or metal ions, can be reactive during a manufacturing process, and can form adducts or other undesirable substances for cell culture in the resulting composition. Hence, the resulting medium after any manufacturing process may be strictly evaluated for physical, chemical and biological evaluation (cell culture growth and performance). Therefore the adaptation of any pelletizing process from the pharmaceutical industry to a cell culture media composition was not straightforward. Manufacture of cell culture media pellets or micro-pellets, either manually or by an automated process has not been done before due to such complexity associated with the process. In fact, even in our own initial attempts at media pelletization, it resulted in undesirable sticky, taffy-like substance, in over-wet media materials with poor flow properties. Exact use of pharmaceutical pellet processes (which are designed for fewer chemicals, drugs) may render the resulting medium or feed useless in that, while good micropellets/pellets are possible, if the pellet cannot maintain cell viability and growth, or cannot sustain/improve cell performance, the end purpose is not achieved. Therefore, until the present invention, there remained a need for pellet media compositions and for methods of making pelletized cell culture compositions (media, feeds, supplements, additives, etc.).

The pelletized media described herein can be obtained by granulating mixed powdered MEDIA components comprising amino acids, sugars, vitamins, trace metal salts, buffers in a process chamber that may be rotating wherein additional powdered media components and/or solvent, may be introduced gradually at a mild temperature. The solvent introduced into the granulating mixed powdered media components can be in the form of a gentle mist, a vapor, dew, a spray, fine droplets, or as a liquid-gas interface.

In one embodiment, the media/feed pellet may be made by a manual process. An exemplary manual method is described in Examples 1 and 2, which may be merely an example of the present teachings, and should not be construed as limiting the scope of how a media/feed pellet can be made manually.

In another embodiment, the media/feed pellet may be made by an automated process. In the automated process, rotor technology can be used in a fluid bed apparatus, also referred to herein as the process chamber. Any rotor/spinning means can be used or adapted in the fluidized process chamber, as would be apparent to one of skill in the art. Use of the term "rotor disc" or "rotor technology" or "atomizer rotor" should not be construed in a limited way. A number of equivalent technologies can achieve similar results: for example, "spinning discs", "spinning disc filtration", "fast spinning pelletizing disk" etc. may also be applied and one of skill in the art would apply the principles accordingly. The configuration of the "rotor" to permit rotation should not be construed in a limited way either; the rollers may be mounted in the fluid bed apparatus in any manner to achieve similar results.

Without being bound by theory, the fluidized system enables formation of fluffy media/feed particles in the fluidized chamber (or process chamber). Starting the pellet formation with media seed particles is not necessary, but can be used if necessary. The additional spinning step of the particles in the chamber causes contacting of the particles with the walls of the vessel and/or the baffles of the vessel, and causing the build-up of powder on to the fluffy particle to form pellets. This is akin to the build-up of snowballs that roll down a hill, accumulating more powdery snow in an avalanche, increasing in size with more and more build-up. As the dry powder particles spin, with the right conditions, there is good size pellets formed. In an exemplary embodiment, the fluidized rotor chamber from Glatt Technologies, NJ was used to make media/feed pellets. Pelletized technology using rotor/fluidized bed chambers are well known in the pharmaceutical industry. However, as indicated before, pharmaceutical compositions comprise a couple to several ingredients within a composition. For example, pharmaceutical compositions may comprise one to a maximum of ten components. On the other hand, cell culture media powders, feed powders, supplement powders used for the cultivation of cells, particularly animal cells, more particularly mammalian cells, and even more particularly, recombinant cells for production of recombinant proteins and vaccines, are highly complex in that they generally comprise 80 to 100 individual components, each of which are required in precise amounts. Some of the media/feed components, like salts or metal ions, can be reactive during a manufacturing process, forming adducts, other undesirable substances. Therefore the adaptation of any pelletizing process from the pharmaceutical industry to a cell culture media composition was not straightforward. Manufacture of cell culture media pellets or micro-pellets, either manually or by an automated process has not been done before due to such complexity associated with the process. In fact, even in our own initial attempts at media pelletization, it resulted in undesirable sticky, taffy-like substance or in over-wet media materials with poor flow properties. Moreover, pharmaceutical pellet processes (which are designed for fewer chemicals, drugs) may render the resulting medium or feed useless in that, while one may obtain good micropellets/pellets, if the pellet cannot maintain cell viability and growth, or cannot sustain/improve cell performance, the end purpose is not achieved. Therefore, until the present invention, there remained a need for pellet media compositions and for methods of making pelletized cell culture compositions.

The pelletized media/feeds described herein differ from agglomerated media described above and in the disclosures mentioned elsewhere (and incorporated by reference) in that they are pelletized due to rotor technology (spinning, particle size build-up) in a spinning chamber, with or without baffles and other means to enhance the process of particle size build-up.

Binders for the pellet compositions described herein may be sticky and lend binding properties to the pellet. A binder may be sugars, any natural binders, or a synthetic or semi-synthetic polymer. Sugars can be used in dry or liquid form, further include but are not limited to glucose (any isomer—D- or L-), sucrose (any isomer—D- or L-), any monosaccharide, disaccharide, oligosaccharide, lactose, maltose, trehalose, or any aromatic sugar. Natural binders can be used in dry, wet or paste forms, and include but are not limited to cellulose, starch, pre-gelatinized starch, non-sugars like acacia, gelatin, alginic acid, tragacanth, and others known in the art. Synthetic or semi-synthetic polymers include but are not limited to methyl cellulose, ethyl cellulose, polyvinyl alcohols, polyvinyl pyrrolidine, polyethylene glycol and others known in the art (the binders are described in pharmaceutical texts and are known in the art, may be used interchangeably hereby incorporated by reference). In certain instances, "excipients" may be added to the base powder before making the pellets. Excipients are inactive substances (that is, they do not impact cell growth or culture) that can serve as a vehicle to provide the other useful substances in the medium to the cell. Excipients can also act as solubility modifiers, as disintegrants, as barriers for coating the media particles (for e.g., film coatings, inert substances, etc). Examples of excipients include but are not limited to polymers or microcrystalline cellulose, crystalline salts, sugars, buffers, etc. Some substances may be considered as binders or as excipients, therefore the term binders and excipients may be used interchangeably in this disclosure, but would be understood by one of skill in the art. In certain embodiments, disintegrants may be introduced into the pellet via the dry powder or the solvent; and may form 1-10% of the pellet particle; disintegrants may include but are not limited to, crosspovidone, cross sodium carboxymethyl cellulose, low substituted hydroxypropylcellulose or the like.

In some embodiments, the spray rate can be a factor for the formation of a pellet from dry powder media or feed. Cell culture feeds, especially media have multiple ingredients (up to 100 components). Some of these ingredients are highly water soluble whereas others are less water soluble, and yet others are sticky or adhesive. This combination of chemical properties presents a challenge for pellet formation of feeds or media (as opposed to fewer combinations in pharmaceuticals). For example, for certain formulations, when too much water may be sprayed on to the dry media/feed powder, or in other formulations, if the spray rate may be too fast, the high water soluble compounds within may begin to dissolve, which may prevent pellet formation. While an optimal level of initial dissolution may be necessary for pellet formation, wetting the mixture initially may cause the powder to become sticky. Again, if optimal, the stickiness can result in good pellets. However, in certain instances, it was observed that too much stickiness (only applicable to certain formulations, due to excess solvent, or fast spray rate, etc.) can result instead in a taffy-like consistency of the dry cell culture components rather than a pellet. For example, in one failed embodiment a base powder comprising microcrystalline cellulose (40%) used 40 gm/min spray rate and resulted in taffy-like consistency of the dry cell culture components rather than a pellet. Based on the teachings described here, one of skill in the art would understand the constraints and be able to obtain pelletized forms of media/feeds using the teachings described in detail and exemplified.

The binders and/or excipients may be blended into the base milled powder and/or may be sprayed into the process chamber with the powder. In examples provided herein, which may not be considered to be limiting, varied conditions were employed to achieve pellets: for example, Pellet Feed 2, Pellet Feed 3, Pellet Feed 4, and Pellet Feed 5 were obtained as detailed below. The pellets thus obtained were evaluated in these assays: 1) physical characteristics (see Microscope pictures and particle size distribution: for example, see FIGS. 3A & B, 4A & B, 5A & B, and 6A & B); 2) and for their analytical content pre- and post-pelletization. This was done by HPLC analysis; that is, media components such as amino acid content, water soluble vitamin content, hydrophobic amino acid content; etc. were analyzed pre- and post-pelletization (data not shown). The analytic data for each of Feeds 2, 3, 4 and 5 were comparable such that the pre- and post-pelletization analytic data did not show significant changes; and 3) for their biological activity, performance in cell culture (see FIGS. 3 to 7; subsection C as applicable, for each Feed pellet).

Media or feed pellets can have a variety of applications in cell culture. For example, in some embodiments, pellet particle sizes ranging from 0-less than about 500 microns can be used in the preparation of water based media/feed suspensions for use in cell culture. In other embodiments, pellet particle sizes ranging from about 800-about 500 microns can be used in the preparation of multi-particulate media/feed tablets for use in cell culture. In yet another embodiment, pellet particle sizes ranging from about 500-about 2000 microns can be used in the preparation of media/feed capsules for use in cell culture.

Applications: The pellets/micro pellets of the invention have potential utility in a wide range of eukaryotic and microbial cell cultures. The pellets/micro pellets of the invention provide several novel delivery options such as: the ability to provide single-unit dosage forms for use in fed-batch systems; the ability for metered-dosing of nutrients for use in perfusion systems; the novel capability to produce modular kits composed of multiple groups of pelleted nutrients (e.g. vitamin pellets, amino acid pellets, etc.); or the ability of the pellet compositions to be surface-coated (with polymer films) for use in controlled release applications. In some embodiments, pellet particle sizes can be controlled for various applications: for example, pellets ranging from 0-less than about 500 microns can be used in the preparation of water based media/feed suspensions for use in cell culture; in other embodiments, pellet particle sizes ranging from about 800-about 500 microns can be used in the preparation of multi-particulate media/feed tablets for use in cell culture; in yet another embodiment, pellet particle sizes ranging from about 500-about 2000 microns can be used in the preparation of media/feed capsules for use in cell culture.

One aspect of the present invention provides dry powder formulations that have undergone pelletization. Another aspect of the invention provides cell culture medium formulations comprising all of the necessary nutritive factors that facilitate the in vitro cultivation of cells. Some embodiments of the invention provide methods and means of producing these pelletized media formulations. Some embodiments of the invention provide methods and means of supplementing these or other media formulations.

A cell culture medium according to the present invention may be any mixture of components which maintains and/or supports the in vitro growth of cells. The cell culture medium can comprise some, parts, or all components necessary to maintain and/or support the in vitro growth of cells. When a cell culture medium only has some components, further components are added separately. Examples of cell culture media according to the present invention are full media which comprise all components necessary to maintain and/or support the in vitro growth of cells, media supplements or feeds. In a preferred embodiment the cell culture medium may be a full medium. There exists a need for new formats of dry powder media.

The cell culture media of the invention can maintain and/or support the growth of cells in a dish, flask, bioreactor, or in any cell culture system or containment such as a disposable bag. In a preferred embodiment, the cell culture medium may be a chemically defined cell culture medium. Chemically defined cell culture media are cell culture media which do not comprise any chemically undefined substances. That means the chemical composition and structure of each chemical used to produce the medium may be known in amount and identity. Chemically defined media do not comprise extracts or hydrolysates of plant, animal, yeast, fungal origin; or it does not comprise serum, serum fractions, conditioned media, digests, cell extracts, feeder cells, or components which may contribute to poor chemical identity of any component in the media. Sometimes, chemically defined media may be defined as comprising defined peptides or defined proteins, in known amounts, of traceable origin.

Definitions

The term "pellet" or "micro-pellets" as used herein refers to "cell culture media compositions" that are compacted by any pelletizing process to improve the appearance, mixing properties, to increase particle size, to avoid dustiness, to prepare a more dense material, to reduce segregation of media components, in general to improve the physical and chemical properties of fine media powders. Dry pellets may also improve powder flowability, and eliminate undesirable properties such as clogging of inlet and outlet ports of any media containers, for example, bioreactors, media bags, media shuttles or media mixer apparatus, etc.

The term "powder" or "dry powder" as used herein refers to media powders or powdered media compositions for cell culture that are present in dry granular form, whose gross appearance may be free flowing. The term "powder" includes agglomerated powders. The term "base powder" or "dry base powder" as used herein generally refers to a starting dry powder composition before it may be pelletized. The term "base powder" or "dry base powder" or "dry powder" may be used interchangeably, and depending on the context, may refer to the starting dry powder before it may be pelletized. It may not mean that the material may be completely free of complexed or agglomerated solvent unless otherwise indicated.

The term "cell culture media compositions" or "powdered media composition" or "media powders" or "dry powder formulations" or "media formulations" may be used interchangeably and broadly include, e.g. a media, media supplement, media subgroup or buffer of the invention and may not be limited to, basal media, complete media, media feeds, media supplements, media additives, concentrated media, concentrated supplements and feeds, amino acids or groups of amino acids, short peptides, vitamins, buffers, salts, trace components, etc. These terms generally refer to components added during cell culture, and the skilled artisan would clearly understand when or how these terms are used.

The term "ingredient" refers to any compound, whether of chemical or biological origin, that can be used in cell culture media to maintain or promote the growth of proliferation of cells. The terms "component," "nutrient" and ingredient" can be used interchangeably and are all meant to refer to such compounds. Typical ingredients that are used in cell culture media include amino acids, salts, metals, sugars, carbohydrates, lipids, nucleic acids, hormones, vitamins, fatty acids, proteins and the like. Other ingredients that promote or maintain cultivation of cells ex vivo can be selected by those of skill in the art, in accordance with the particular need.

The phrases "cell culture medium," "culture medium," and "medium formulation" (plural "media" in each case) refer to a nutritive solution that supports the cultivation and/or growth of cells; these phrases may be used interchangeably. Cell culture medium may be a basal medium (a general medium that requires additional ingredients to support cell growth) or a complete medium that has all or almost all components to support cell growth. Cell culture media may be serum-free, protein-free (one or both), may or may not require additional components like growth factors, additives, feeds, supplements, for efficient and robust cell performance.

The term "combining" refers to the mixing or admixing of ingredients in a cell culture medium formulation. Combining can occur in liquid or powder form or with one or more powders and one or more liquids. In another example, two or more powdered components may be mixed and then agglomerated to produce a complex mixture such as media, media supplements, media subgroups or buffers.

The term "contacting" refers to the placing of cells to be cultivated into a culture vessel with the medium in which the cells are to be cultivated. The term "contacting" encompasses inter alia mixing cells with medium, perfusing cells with medium, pipetting medium onto cells in a culture vessel, and submerging cells in culture medium. "Fed-Batch" defines a method of supplying the compositions of the instant invention to cells such that the concentration of a reagent is additive of the individual additions of the reagent.

A feed or a supplement when added to cells in standard culture may be beneficial for its maintenance, or expansion, or growth, or viability, or affects its cell performance, or increases culture longevity or maintaining cells in a pseudo-stationary phase wherein product expression continues, or results in a significant increase in final product titer. A feed or supplement may be used interchangeably in this disclosure and refers to powdered and liquid formats (including agglomerated formats) of media components comprising one or more amino acids, sugars, vitamins, buffers, sometimes, peptides, hydrolysates, fractions, growth factors, hormones, etc. required to rebalance or replenish or to modulate the growth or performance of a cell in culture, or a cell culture system. A feed or supplement may be distinguished from a cell culture medium in that it is added to a cell culture medium that can culture a cell. As would be understood by one of skill in the art, sometimes a feed/supplement may comprise mainly those amino acids, sugars, vitamins, buffers, etc. required to rebalance or replenish or modulate the growth or performance of a cell in culture, or a cell culture system. A feed or supplement may or may not be concentrated, or may be partially concentrated for certain components only. The term "feed" or "supplement" which when added to standard cell culture media, enhances cell growth, culture longevity and product expression. Examples are given showing where supplement may be particularly effective in production of antibodies. Alternately, feeds or supplements may be used for hybridoma cell lines, cell lines that culture viruses for vaccine production, etc.

The term "cell performance" means culturing a cell in vitro and evaluating by any standard parameter known to one of skill in the art, including but not limited to measurement of one of more of: cell viability, cell count/number, protein expression, DNA estimation, protein titer measurement, recombinant polypeptide or protein production, polypeptide or protein production secretion, virus or viral particle production, a secreted protein, whether cells produce/secrete a protein of interest, detection of cell markers, whether cell is in suspension or is attached cell, etc. In general, cell performance is evaluated as when the final product may be increased due to the addition or change in format (for e.g. pellet, over control (liquid) format; culture with feed or without feed, etc.).

By solvent is meant water (distilled and/or deionized water, Gibco® Water for Injection (WFI) for Cell Culture may be high quality, cell culture grade water that complies with both United States Pharmacopoeia (USP) and European Pharmacopoeia (EP)), buffers, acids or bases (pH adjusting agents), any of which may contain one or more additional components (e.g., salts, polysaccharides, ions, detergents, stabilizers, etc.).

Particle size of the pellets may be quantified by laser light scattering or by mechanical segregation on relative mesh size calibrated screens. In general, particle size may be expressed in microns, millimeters or in mesh size, following standardized U.S. measurements—a comparative conversion table is provided below. The pellets obtained by the methods described in this disclosure may be of various sizes; in some instances, the pellet has a size of about 0.05 mm to 7 mm. In a particular aspect the invention provides pellets having a size of about 0.05 mm to about 0.5 mm, or about 0.05 mm to about 1 mm, or about 0.05 mm to about 2 mm, or about 0.05 mm to about 3 mm, or about 0.05 mm to about 4 mm, or about 0.05 mm to about 5 mm, or about 0.05 mm to about 6 mm, or about 0.05 mm to about 0.1 mm, or about 0.05 mm to about 0.2 mm, or about 0.05 mm to about 0.3 mm, or about 0.05 mm to about 0.4 mm, or about 0.1 mm to about 1 mm, or about 0.1 mm to about 2 mm, or about 0.1 mm to about 3 mm, or about 0.1 mm to about 4 mm, or about 0.1 mm to about 5 mm, or about 0.1 mm to about 6 mm, or about 0.5 mm to about 1 mm, or about 0.5 mm to about 2 mm, or about 0.5 mm to about 3 mm, or about 0.5 mm to about 4 mm, or about 0.5 mm to about 5 mm, or about 0.5 mm to about 6 mm, or about 0.5 mm to about 7 mm, or about 1 mm to about 2 mm, or about 1 mm to about 3 mm, or about 1 mm to about 4 mm, or about 1 mm to about 5 mm, or about 1 mm to about 6 mm, or about 1 mm to about 7 mm. In a particular embodiment, the invention provides pellet preparations mostly having a size pellet size may be larger than about 0.1 mm, or larger than about 0.2 mm, or larger than about 0.3 mm, or larger than about 0.4 mm, or larger than about 0.5 mm, or larger than about 0.6 mm, or larger than about 0.7 mm, or larger than about 0.8 mm, or larger than about 0.9 mm, or larger than about 1 mm, or larger than about 2 mm.

TABLE 1

| U.S. particle size | | |
| --- | --- | --- |
| Micron | U.S. Mesh | Inches |
| 2000 | 10 | 0.0787 |
| 1680 | 12 | 0.0661 |
| 1410 | 14 | 0.0555 |
| 1190 | 16 | 0.0469 |
| 1000 | 18 | 0.0394 |
| 841 | 20 | 0.0331 |
| 707 | 25 | 0.028 |
| 595 | 30 | 0.0232 |
| 500 | 35 | 0.0197 |
| 420 | 40 | 0.0165 |
| 354 | 45 | 0.0138 |
| 297 | 50 | 0.0117 |
| 250 | 60 | 0.0098 |
| 210 | 70 | 0.0083 |
| 177 | 80 | 0.007 |
| 149 | 100 | 0.0059 |
| 125 | 120 | 0.0049 |
| 105 | 140 | 0.0041 |
| 88 | 170 | 0.0035 |
| 74 | 200 | 0.0029 |
| 63 | 230 | 0.0024 |
| 53 | 270 | 0.0021 |
| 44 | 325 | 0.0017 |
| 37 | 400 | 0.0015 |

Formulations of media, media feeds/supplements and media subgroups to be pelletized, as well as many other commonly used animal cell culture media, are well-known in the art and may be found, for example, in the GIBCO/BRL Catalogue and Reference Guide (Invitrogen Corporation Carlsbad Calif.) and in the Sigma Animal Cell Catalogue (Sigma; St. Louis, Mo.).

Agglomerated media and their preparations, especially for use in cell culture have been well described. Fluid bed technology produces agglomerated powders having altered characteristics (particularly, for example, solubility) from the starting materials. In general applications of the technology, powders are suspended in an upwardly moving column of air while at the same time a controlled and defined amount of liquid may be injected into the powder stream to produce a moistened state of the powder; mild heat may be then used to dry the material, producing an agglomerated powder. Preparation of agglomerated media/feeds, nutritive powders, supplements, etc., their properties, methods to prepare auto pH and auto osmolarity of agglomerated media/feeds, nutritive powders, supplements, etc. have been described in detail in prior applications/patents: for example, in U.S. application Ser. Nos. 09/023,790; 11/669,827; 13/984,263; PCT/US 2012/024194; EP application 10175914.0; EP publication 2778221, and their disclosures are hereby incorporated by reference in their entirety. Methods to analyze bulk density, angle of repose, particle size of agglomerated media are well described for example, in U.S. application Ser. No. 11/669,827, which is hereby incorporated by reference in its entirety.

The media/feeds to be pelletized may have a pH that may be optimal for the support of cell cultivation or growth without a need for adjustment of the pH of the liquid medium. This type of medium, defined herein as "automatically pH-adjusting medium," therefore obviates the time-consuming and error-prone steps of adding buffer(s) to the medium after reconstitution and adjusting the pH of the medium after dissolution of the buffer(s) and has been well described in U.S. application Ser. No. 11/669,827, which is hereby incorporated by reference in its entirety. For example, a mammalian cell culture medium prepared according to these methods may, upon reconstitution, have a pH of between about 7.1 to about 7.5, more preferably between about 7.1 to about 7.4, and most preferably about 7.2 to about 7.4 or about 7.2 to about 7.3. An auto-pH medium maybe provided by adjusting the buffering systems present within the medium itself, for example, opposing forms of conjugate acid-base amino acids. By adjusting the pH-opposing forms of such buffers in the medium, the invention provides for production of an auto-pH medium, avoiding the requirement to add additional buffers or pH-adjusting agents to achieve a proper pH level prior to or upon reconstitution of the medium and prior to use. For example, Sodium HEPES (pH raising) and HEPES-HCl (pH lowering) are examples of pH opposing components. Monobasic, dibasic and/or tribasic buffer salts are other examples of pH opposing components. Typically, mono, dibasic and tribasic phosphate salts are used, but other salts may also be used in proper ratios.

"Microsuspensions": Cell culture media component(s) or the base powder may be dissolved, suspended, colloided or otherwise introduced into a solvent at a desired concentration, prior to use for pelletization (see Example 1).

Methods of growing cells employing the media supplements described herein such that they can be included in medium at the start of culture, or can be added in a fed-batch or in a continuous manner. The resulting media can be used in various cultivation methods including, but not limited to, batch, fed-batch, chemostat and perfusion, and with various cell culture hardware including, but not limited to, stationary flasks, agitated flasks, spinner flasks, stirred fermentors, airlift fermentors, membrane reactors (including hollow fiber, flat membrane plate, external loop perfusion), reactor s with cells retained on a solid support or immobilized/entrapped as in microporous beads, and any other configuration appropriate for the growth or maintenance of the desired cell line.

Cell lines that can be grown in reconstituted liquid media from pellets may be eukaryotic, prokaryotic, animal, plant, fungal, algal, insect, or yeast cells or cells used for the cultivation of a virus or a viral particle. Exemplary cells include but are not limited to keratinocytes, endothelial cells, hepatocytes, melanocytes, CHO cells, BHK cells, VERO, 293 cells, PerC6, hybridomas, hematopoetic cells, embryonic cells, neural cells etc.

Additional components to be added in low amounts to the culture media of the invention may or may not be included as needed, for example, serum or serum fractions, growth factors (e.g., EGF, aFGF, bFGF, KGF, HGF, IGF-1, IGF-2, NGF, insulin, and the like), interleukins, colony-stimulating factors, interferons, attachment factors, extracellular matrix components (e.g., collagens, laminins, proteoglycans, glysoaminoglycans, fibronectin, vitronectin, and the like), lipids (such as phospholipids, cholesterol, bovine cholesterol concentrate, fatty acids, sphingolipids and the like), peptides (for e.g.: di, tri, tetra peptides), purified or recombinantly expressed proteins (e.g.: recombinant albumin, recombinant insulin), hydrolysates (e.g., plant like rice, yeast, corn, potato), etc.

EXAMPLES

The novel features of the invention are set forth with particularity in the appended claims. A better understanding of the features and advantages of the present invention will be obtained by reference to the following examples in which the principles of the invention are utilized. The skilled artisan will understand that the examples described herein are merely aspects of the present teachings, and should not be construed as limiting the scope of the present teachings in any way.

Making Pellets of Cell Culture Media, Feeds, Supplements or Buffers

Described herein are exemplary protocols for making pellets from a dry powder of cell culture medium, feed, buffer or supplement. The principles used in these procedures and the equipment mentioned herein may be applied broadly by one of skill in the art to obtain any pellet composition.

Example 1: Manual Method of Making Pellets From Microsuspensions

Figure 1B:
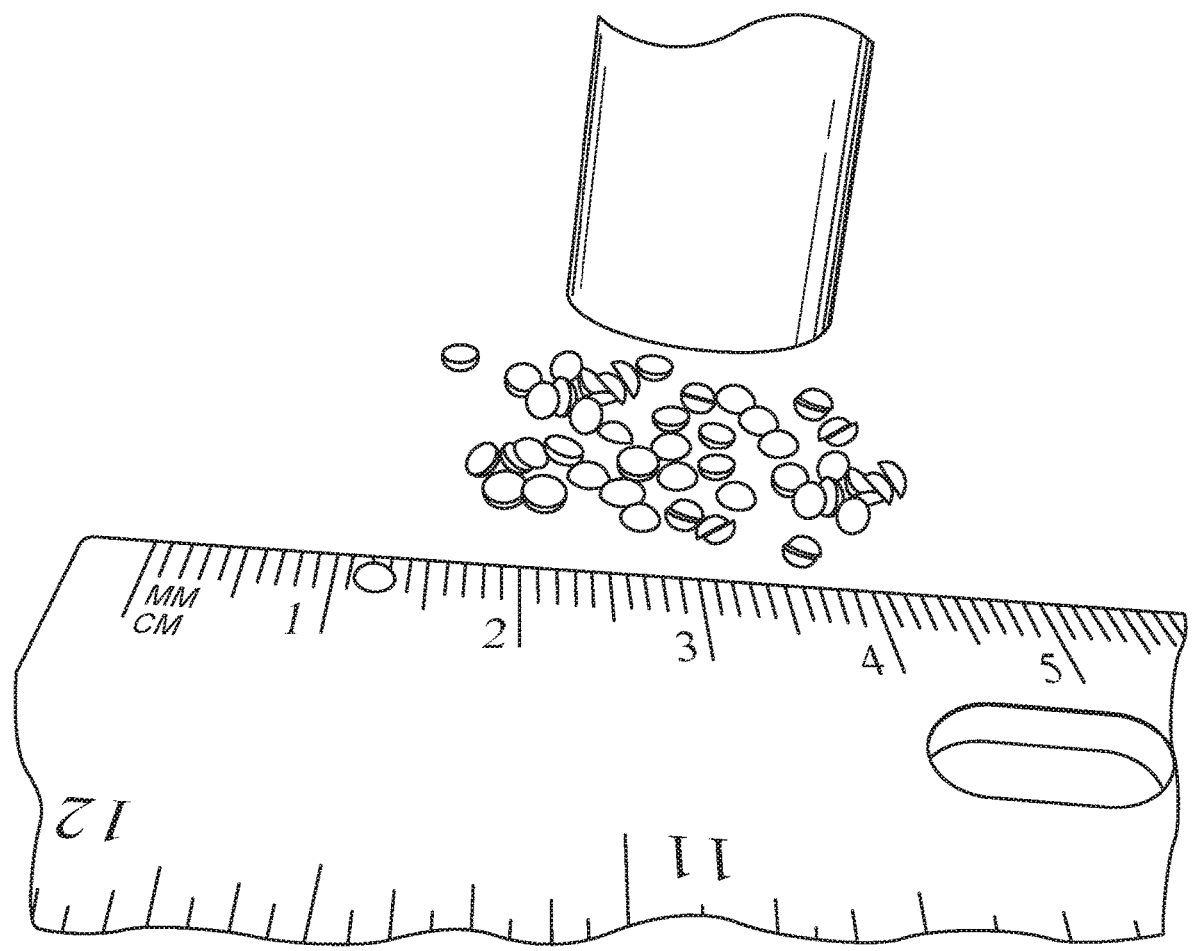
Figure 1C:
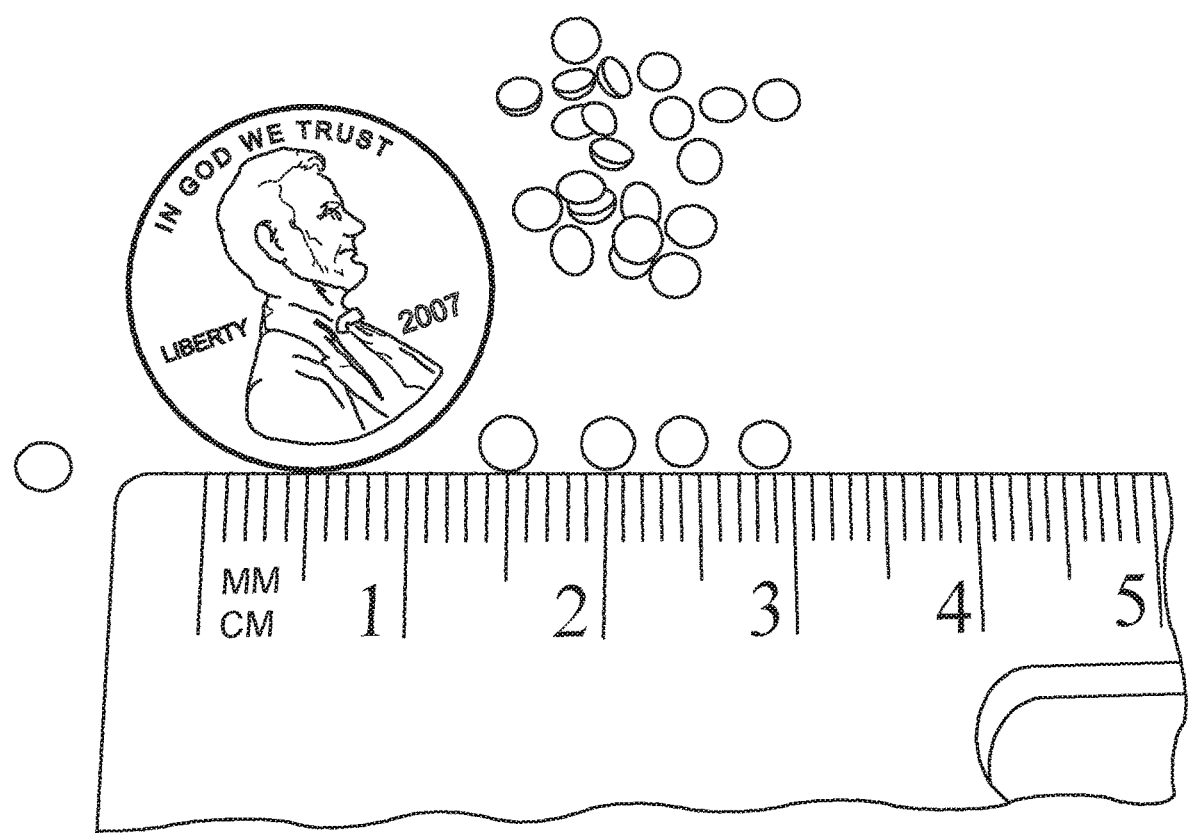
Figure 9B:
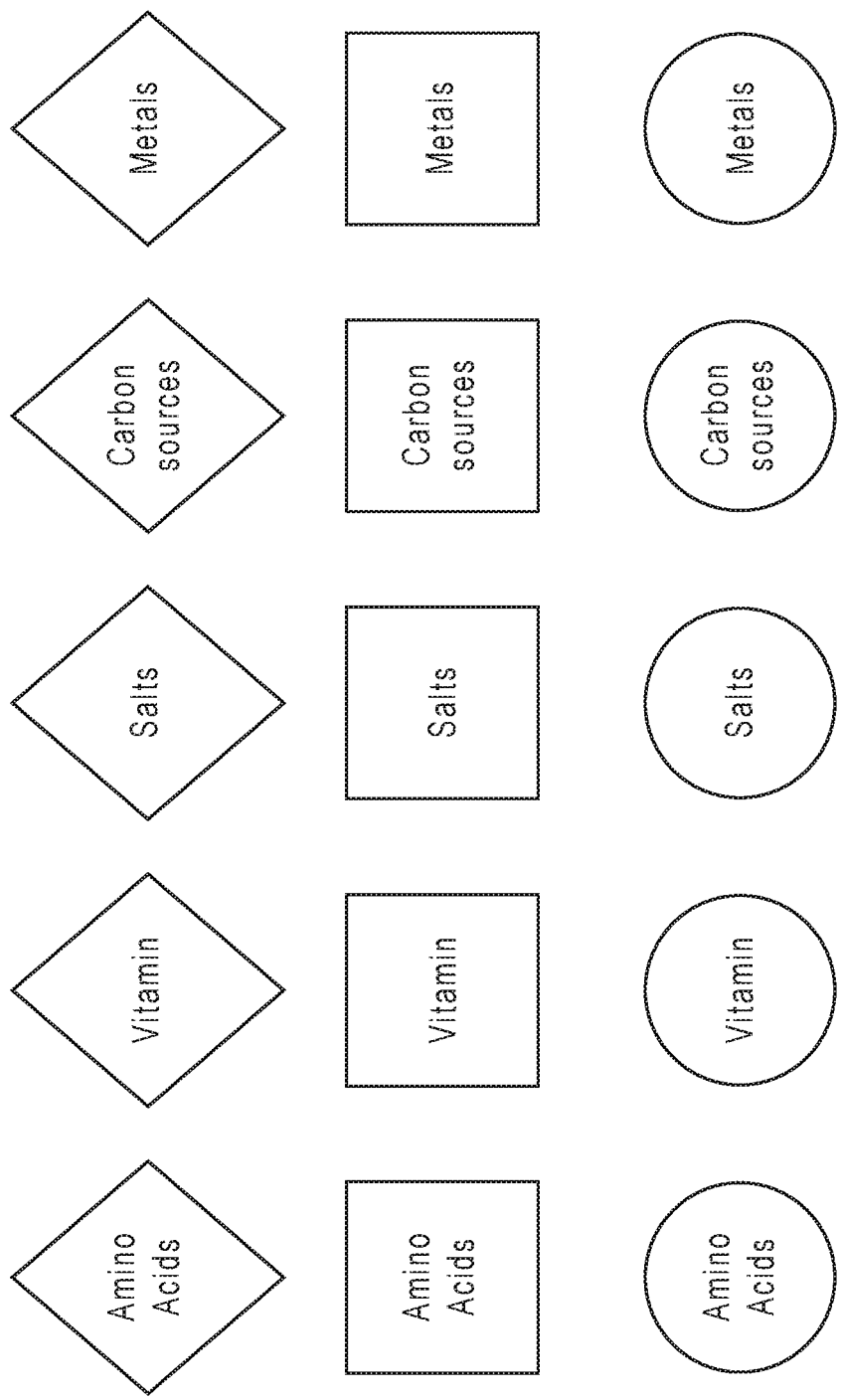
Figure 10:
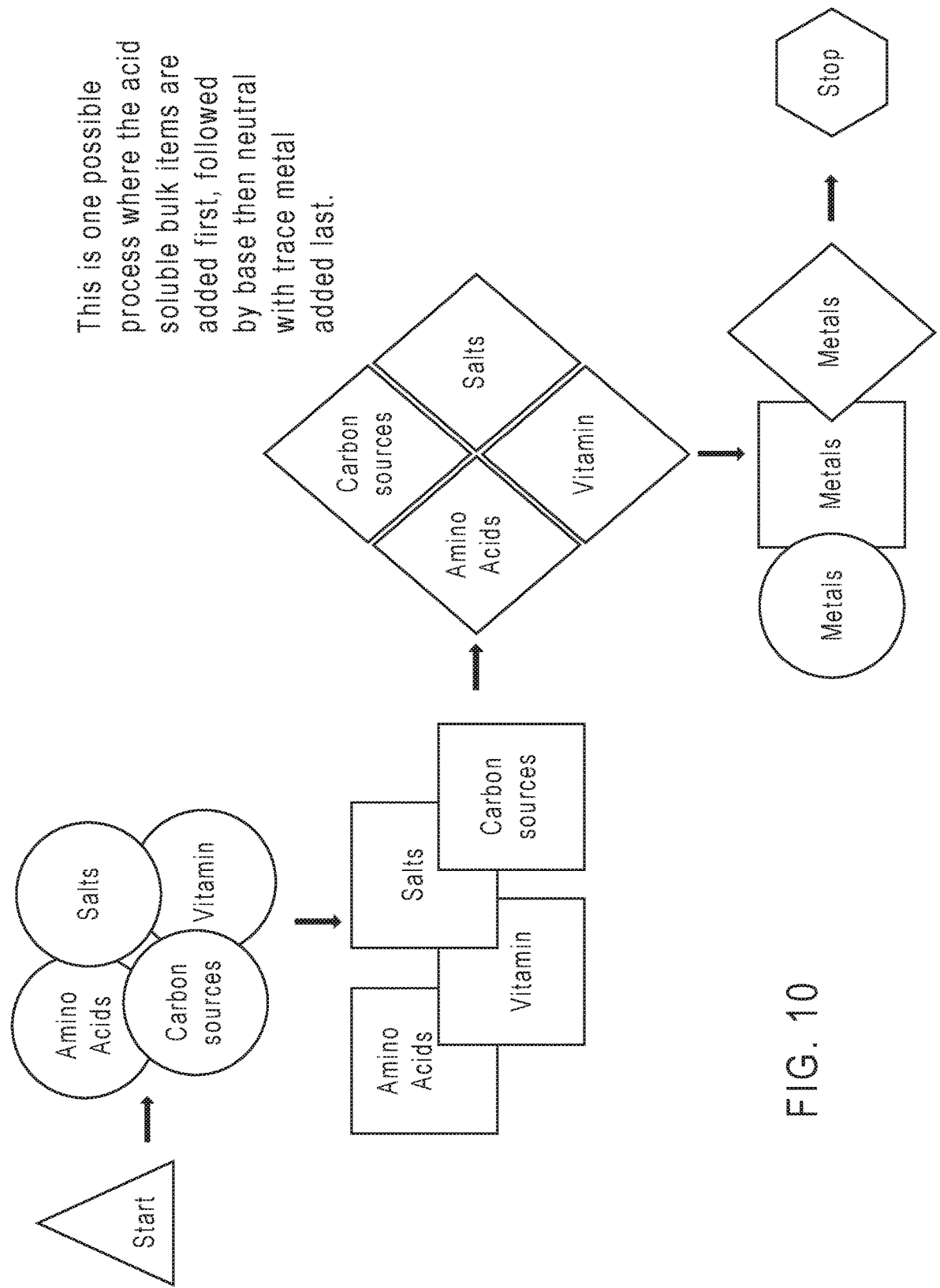
FIG. 10: An exemplary process for making modular media wherein the acid soluble (bulk) items are added first, followed by the base neutral items, and finally, followed with the trace metal items. In one embodiment, each item (acid soluble, base soluble or neutral soluble) may be individually pelleted. In another embodiment, the items are added sequentially as powders and then pellet together to form a composite pellet. In yet other embodiments, an individual acid soluble item or a combination of acid soluble items, like a particular acid soluble amino acid, or a combination of amino acids, or individual or combination of base soluble items, or individual or combination of neutral soluble may be formed into pellets. Note, the sequential order of addition (acid soluble first, base soluble next or neutral soluble last) described herein is only exemplary. The order of addition or mixing can be changed as desired, and may depend on the formulation or the presence of components that react adversely.

A manual method for pelletizing a feed using an extrusion process is presented herein.
1) In this example, catalog product Efficient Feed B AGT (also called Feed 1 in the FIGS. 1 and 2) [Thermo Fisher catalog number, agglomerated, # A2530] was the starting base milled powder. Weigh 30 g of Efficient Feed B AGT (without sodium phosphate was used here) into a mortar. Phosphates may be included in formulation.
2) Add 12.5 ml WFI (water).
3) Using green plastic pliable spatula, mix until the powder is wetted and begins to "take up" the water and form a paste. Thoroughly rapidly mix the paste for homogeneity.
4) If needed to make a viscous but flowable mixture, add WFI to microsuspensions and mix thoroughly. Wet mill if needed with motor and pestle. Wet-milling makes the microsuspension more homogeneous and reduces air bubbles caused by vigorous mixing.
5) Collect into container; use spatula to "squeegee" the last amount of microsuspensions into container (volume will be ~29-30 ml).
6) Prepare Eppendorf Repeater-Plus with 0.5 ml syringe by cutting the end by ~1/64" with scissors while making sure that the cut is not as far as the location of the end of plunger when fully depressed.
7) Using Eppendorf Repeater-Plus with 0.5 ml syringe set at position 0.5 (5 µl), slowly pull microsuspension up into syringe. Make sure that air is not aspirated into the syringe as this would remain in the viscous microsuspension and alter the volume delivered.
8) Depress Eppendorf lever several times to prime syringe. After microsuspension flows out of the syringe end, wipe off end of syringe. Then hold syringe end vertically close to a solid hydrophobic surface (e.g., parafilm or waxed paper), depress lever and gently place the droplet onto the surface. Immediately lift, depress lever again and repeat. Replicates can be done in a very rapid manner.
9) Place under fume hood 18 to 24 hours. See FIGS. 1A, 1B, 1C and legends.
10) Collect pellets, place into weighing pan and place into vacuum drying chamber over $CaSO_4$.
11) Let pellets dry for 48 to 72 hours. The pellets obtained thereof are referred to as Pellet Feed 1, or Feed 1, or Feed 1 pellet, sometimes used interchangeably. 0.156 g beads were produced from 3.0 ml of Efficient Feed B supplement. See FIGS. 1A, 1B, and 1C for pictures of the pellets. The size of the beads appeared uniform and measured in the millimeter range. The beads were used for viability, growth and performance (protein titer) assays as described in Example 4.

Example 2: Biological Evaluation of Manually Prepared Feed 1 Pellets

The Feed 1 beads were prepared (see Example 1) and were used in cell viability, growth and performance (protein titer) assays. Feed 1 pellet/beads results were compared to liquid supplement (the positive control; that is # A2530 reconstituted in liquid and sterile filtered before use). For the assays, DG44-IgG cell line was grown in CD-OptiCHO medium (Thermo Fisher Catalogue #12681). The culture was/was not supplemented (as indicated) with Efficient Feed B (EFB) (Thermo Fisher Catalogue # A2530) or Feed 1 either in pellet format (sometimes referred to as bead), or as a liquid (positive control). Cells were sub-passaged three times for 3 days, and with each sub-passage, cells were split into $3 \times 10 e^5$ viable cells/ml. At the $4^{th}$ sub-passage, daily cell counts were taken. Each condition was performed in triplicate (that is, curves 1, 2, 3 are triplicates for each type supplement. In FIG. 2A, viability of manually prepared pellets (the test sample) are shown in curves bead 1, 2, 3; Viability of liquid (the positive control) are shown as liq 1, 2, 3; Viability of un-supplemented (negative control) is shown in Neg. cont. 1, 2, 3. The EFB beads/pellet concentrations were equimolar as compared to EFB liquid format. As seen in FIG. 2A, cell culture supplemented with beads/pellet EFB (1, 2, 3) showed better % viability compared to cell culture supplemented with liquid EFB (1, 2, 3), especially from day 8 to 16.

Feed 1 pellet/beads were compared to liquid supplement (the positive control) in cell growth assays—FIG. 2B. Here too, DG44-IgG cell lines in CD-OptiCHO medium (Thermo Fisher Catalogue #12681) was used. Cells were sub-passaged and split as described above for 2A. At the $4^{th}$ sub-passage, daily cell counts were taken. Each condition was performed in triplicate (that is, curves 1, 2, 3 are triplicates for each condition. In FIG. 2B growth of manual pellets (the test sample) are shown in curves bead 1, 2, 3; Growth curves of liquid (the positive control) is shown in Liq. 1, 2, 3; Growth curves of un-supplemented (negative control) are shown in Neg. cont. 1, 2, 3. The EFB beads/pellet concentrations were equimolar as compared to EFB liquid format. As seen in FIG. 2B, cell culture supplemented with beads/pellet (1, 2, 3) showed comparable cell growth over a period of 15 days in culture as compared to cell culture supplemented with liquid (1, 2, 3).

Feed 1 pellet/beads were compared to liquid supplement (the positive control) in cell performance or protein titer assays (measure antibody production)—FIG. 2C. Here too, DG44-IgG cell lines in CD-OptiCHO medium (Thermo Fisher Catalogue #12681) was used. Cells were sub-passaged and split as described above for 2A. At the $4^{th}$ sub-passage, daily cell counts were taken and IgG production was monitored. Each condition was performed in triplicate (that is, curves 1, 2, 3 are triplicates for each condition. As seen in FIG. 2C, protein titers (cell performance) of manual pellets are shown in curves bead 1, 2, 3; Protein titers of liquid (the positive control) is shown in Liq. 1, 2, 3; Protein titers of un-supplemented (negative control) are shown in Neg. cont. 1, 2, 3. As seen in FIG. 2C, cell culture supplemented with bead/pellet 1, 2, 3 showed IgG production ~325 µg/ml (production) slightly lower than IgG produced at ~425 µg/ml with the positive liquid control EFB (1, 2, 3) over a period of 15 days in culture. Un-supplemented negative control showed much lower IgG of ~100 µg/ml when compared to cell culture supplemented with EFB beads (test).

Example 3: Exemplary Automatic Fluid Bed Pelletization Process

An exemplary automated process for making pellets is presented herein. Here, rotor technology was used in a fluid bed apparatus/process chamber (for e.g., Glatt Technologies, NJ). Any spinning process chamber with fluid bed attachments can be adapted for making cell culture media pellets. A starting dry powder (cell culture media, feed, etc.) was charged onto the rotor disk of the fluid bed apparatus which moved by spinning and the air flowed into the fluid bed apparatus. In this instance, liquid was carefully introduced (for e.g., a fine spray, a mist, a vapor, dew, a condensation, or minute droplets) at a controlled rate, sometimes intermittently, at a controlled temperature, such that pellet formation of the dry powder occurred. Typically, other automatic equipment may also be used to make the pellet; these include but are not limited to: milling equipment, micronizer, a fluid bed processor, spinning disc rotor, sprayers for the solvent, etc. See FIG. 8 for an exemplary workflow for pelletization of media. In a particular embodiment, pellets were formed as follows:

a. Start with milled dry base powder (not granulated). Optionally, the base powder may be pre-wetted with a suitable solvent. The dry powder may or may not contain a binder and/or excipient. In addition, the solvent to be sprayed may or may not contain a binder and/or excipient.

b. If no binder and/or excipient is present in dry base powder, or alternately, if more binder and/or excipient (than what is present in the base powder) is necessary to form the pellet, the solvent solution to be sprayed will contain the appropriate amount of and/or excipient.

c. Exemplary process parameters for obtaining cell culture feed pellets are described herein. These parameters were chosen for the formulations tested.

i. Spray Rate: most preferably 5 gm/min (spray rate ranges: about 1 gm/min up to about 30 gm/min, depending on the formulation)

ii. Inlet Temp—25° C. (20-25° C.)

iii. Product Temp—(20-30° C.) (because the media/feed contains temperature sensitive components)

iv. Air volume (30-40 m³/hr)

v. Atomization Air Pressure—2 bar vi. Drying temp for pellets (50-60° C.) (because the media contains temperature sensitive components) in the fluid bed processor.

Example 4: Exemplary Media Preparations Used for the Automated Pelletizing Process The following media compositions were used to prepare pellets in an automated system. These compositions serve merely as examples and should not be construed as limiting.

Thermo Fisher Catalogue product, PL002616P1 was the starting dry base powder for preparing Pellet Feed 2, Pellet Feed 3, Pellet Feed 4, and Pellet Feed 5. Exemplary feeds as described below were tested for pelletization:

| | |
|---|---|
| Amino Acids | 25-35% |
| Dextrose | 40-65% |
| Vitamins | 1-5% |

| | |
|---|---|
| Salts | 3-5% |
| Trace components | 0.01-0.05% |
| TOTAL | 100% |

The pellets may or may not comprise binders and/or excipients, which may be blended into the base milled powder and/or may be sprayed into the process chamber with the powder. Varied conditions were employed to achieve pellets: Pellet Feed 2, Pellet Feed 3, Pellet Feed 4, and Pellet Feed 5 as detailed below. The pellets thus obtained were evaluated in three types of assay: 1) physical characteristics (see Microscope pictures and particle size distribution: FIGS. 3A & B, 4A & B, 5A & B, and 6A & B); 2); for their analytical content pre- and post-pelletization. The feed pellets were tested by HPLC for chemical composition and compared to the milled powder starting material. HPLC analysis for media components such as amino acid content, water soluble vitamin content, hydrophobic amino acid content; etc. (data not shown), indicated that the multiple ingredients in the feed medium remained within acceptable range after undergoing process and drying steps during pelletization. The pre- and post-pelletization analytic data for each of Feeds 2, 3, 4 and 5 were comparable; and 3) for their biological activity, performance in cell culture (see FIGS. 3 to 7; subsection C as applicable, for each feed pellet).

Media or feed pellets can have a variety of applications in cell culture. For example, in some embodiments, pellet particle sizes ranging from 0-less than about 500 microns can be used in the preparation of water based media/feed suspensions for use in cell culture. In other embodiments, pellet particle sizes ranging from about 800-about 500 microns can be used in the preparation of multi-particulate media/feed tablets for use in cell culture. In yet another embodiment, pellet particle sizes ranging from about 500-about 2000 microns can be used in the preparation of media/feed capsules for use in cell culture. An exemplary formulation for the preparation of such pelletized feeds is proposed below:

| | |
|---|---|
| Amino Acids | 20.710% |
| dextrose | 28.610% |
| Vitamins | 0.010% |
| Salts | 36.480% |
| Organics | 13.150% |
| Trace components | 0.001% |
| TOTAL | 98.961% |

Example 5: Exemplary Methods to Measure Physical Characteristics of Powders

An Exemplary Method for Flow Analysis Procedure

This procedure can be used for flow analysis and measurements that can be determined include FRI (Flow Rate Index); FDI (Feed Density Index); BDI (Bin Density Index); and SPI (Spring Density Index).

1. Assemble indicizer (any flow rate indicizer system for e.g.: from Johanson Innovations, Inc, San Luis Obispo, Calif.) sample container by placing a suitable mesh screen clamped onto the support insert in bottom of sample cup.
2. Tare the indicizer sample container on appropriate balance.
3. Place approximately 100 gram sample into suitable container and aerate by mixing the sample with a spoon or whisk.
4. Using a spatula, remove a portion of the sample and gently place the sample into the assembled indicizer sample container, avoiding compacting the sample.
5. Repeat addition of sample until pellet sample is overflowing/above the indicizer sample container.
6. Gently level the pellet sample to the top of the indicizer sample container by scraping off the excess.
7. Weigh and record sample weight of pellet sample in the indicizer sample container using already tared balance.
8. Place the sample container onto the indicizer and attach the air-lines to the sample container.
9. Set processing parameters on indicizer for Bin Angle, Outlet diameter, and Bin diameter. After the test is complete, record indicizer output.

An Exemplary Procedure for Measuring Angle of Repose

1. Place approximately 50 grams of sample into a suitable container and aerate by mixing the sample with a spoon or whisk.
2. Set rectangle powder bed box onto support platform.
3. Ensure that support platform is set at 0 (zero) degree angle, read at bottom of platform.
4. Pour material through the funnel into rectangle powder bed box until material begins to touch at least one of the box's sidewall and forms a cone.
5. Slowly and constantly raise the sample bed box and platform using the support screw ensuring as smooth a transition as possible.
6. As soon as the peak of the material shifts, stop rotating the support screw, and take the angle of repose measurement using the device's protractor, reading the protractor's angle at the base of the support platform.

Example 6: Fluid Bed Automatic Pelletization Using Rotor Technology—Production of Pellet Feed 2

Feed 2 pellets/beads were prepared in an automated process as described below:
1. Started with milled dry base powder (not granulated) Thermo Fisher Catalog # PL002616P1—950.0 g (Net Weight). Optionally, the base powder can be pre-wetted in certain embodiments; not done here.
2. Loaded the powder into a fluid bed processor equipped with a rotor disc.
3. Turn-on fluid bed processor to pre-set conditions (identified during development runs) to begin direct pelletization from powder. Parameters are controlled (for e.g., air volume, atomization air pressure, flow rate, inlet temperature, outlet temperature, product temperature, solvent spray rate, rotor disk speed, disk gap, disk shape air volume, atomization air pressure flow rate, inlet temperature, outlet temperature, product temperature, solvent spray rate, rotor disk speed, disk gap, disk shape, etc.)
4. Monitor pellet formation by taking in-process sample measurements (e.g., microscopy FIG. 3A; other physical properties=Table 2; particle size FIG. 3B and Table 3 below) to determine when process is complete.
5. Discharge wet pellets (805.0 g Total Weight) from fluid bed processor.
6. Dry the wet pellets perform physical properties analysis (Table 2).
7. Remove approximately 50.0 g of pellets for particle size measurement (Table 3).

Physical Characteristics Evaluation of Automated Method Pellet Feed 2

TABLE 2

Pellet Feed 2: Physical Characteristics

| Material | Weight (g) | Loss on drying (%) | bulk density (g/cc) | Angle of Repose |
|---|---|---|---|---|
| milled powder | 950 | — | 0.719 | 37.8 |
| wet pellets | 805 | — | — | — |
| dry pellets | 800.4 | 2.07 | 0.53 | 34.7 |

An Angle of repose below 50° (34.7) indicates that Pellet Feed 2 has good flowability. The bulk density indicates that the particles can be compacted, if desired.

TABLE 3

Pellet Feed 2. Particle Size Analysis

| Mesh # | Size Retained (microns) | Amount Retained (g) | percent Retained |
|---|---|---|---|
| 20 | 840 | 8.9 | 17.8 |
| 30 | 600 | 21.4 | 42.8 |
| 40 | 420 | 13.6 | 27.2 |
| 60 | 250 | 3.6 | 7.2 |
| 80 | 177 | 0.7 | 1.4 |
| 100 | 150 | 0.9 | 1.8 |
| Pan | <150 | 0.9 | 1.8 |
| Total | — | 50 | — |

The particle size analysis for Feed 2 indicates that about 95% of the particles are greater than 60 mesh, whereas about 87.8% of the particles are greater than 40 mesh, or about 87.8%>0.4 mm.

Feed 2 beads were then evaluated in cell viability, growth and performance (protein titer) assays. Feed 2 pellet/beads results were compared to liquid supplement (the positive control), that is Thermo Fisher Catalog # PL002616P1 reconstituted in liquid and sterile filtered before use. For the assays, DG44-IgG cell line was grown in CD-CHO medium (Thermo Fisher Catalogue #12490). The culture was/was not supplemented (as indicated) with Thermo Fisher Catalog # PL002616P1—either in pellet format (sometimes referred to as bead), or as a liquid (positive control). Cells were sub-passaged three times for 3 days, and with each sub-passage, cells were split into 3×10 e$^5$ viable cells/ml. At the 4$^{th}$ sub-passage, daily cell counts were taken.

Automated Feed 2 pellet/beads were compared to liquid supplement (the positive control) in cell growth assays—FIG. 3C. Cell culture supplemented with beads/pellet showed comparable cell growth over a period of 15 days in culture as compared to cell culture supplemented with liquid. Pellet Feed 2 showed viable cell counts ~10×10 e$^6$ cells/ml (growth) slightly higher than cell culture supplemented with Positive Control Feed (~8×10 e$^6$).

Viability assays were performed for Pellet Feeds 2 and compared to positive (with liquid feed supplementation) or negative controls (no liquid or pellet supplementation)—FIG. 7A. As seen from the graphs in 7A, Feeds 2, 3 and 4 compared well, like the positive control and better than the negative control, especially after day 6.

Cell performance (antibody production) assays were performed for Pellet Feeds 2, and compared to positive (with liquid feed supplementation) or negative controls (no liquid or pellet supplementation)—FIG. 7B. As seen from the graph 7B, Feeds 2 compared well, like the positive control and better than the negative control, especially after day 4. Cell culture supplemented with Pellet Feed 2 (~229 µg/ml) showed IgG production comparable with IgG produced ~228 µg/ml (at day 14) with the Positive Control Feed; the un-supplemented cell culture assay (negative control) showed much lower IgG (~100 µg/ml) when compared with cell culture supplemented with Pellet Feed 2.

Example 7: Fluid Bed Automatic Pelletization Using Rotor Technology—Production of Pellet Feed 3

Feed 3 pellets/beads were prepared in an automated process as described below.
1. Started with milled dry base powder (not granulated) Thermo Fisher Catalog # PL002616P1—950.0 g (Net Weight). Optionally, the base powder can be pre-wetted in certain embodiments; not done here.
2. Loaded the powder into a fluid bed processor equipped with a rotor disc.
3. Turn-on fluid bed processor to pre-set conditions (identified during development runs) to begin direct pelletization from powder. (e.g., air volume, atomization air pressure flow rate, inlet temperature, outlet temperature, product temperature, solvent spray rate, rotor disk speed, disk gap, disk shape etc.)
4. Monitor pellet formation by taking in-process sample measurements (e.g., microscopy FIG. 4A; other physical properties=Table 4; particle size FIG. 4B and Table 5 below) to determine when process is complete. Discharge wet pellets (770.0 g Total Weight) from fluid bed processor.
5. Dry the wet pellets perform physical properties analysis (Table 4).
6. Remove approximately 50.0 g of pellets for particle size measurement (Table 5).

TABLE 4

Pellet Feed 3: Physical Characteristics

| Material | Weight (g) | Loss on drying (%) | bulk density (g/cc) | Angle of Repose |
|---|---|---|---|---|
| milled powder | 950 | — | 0.719 | 37.8 |
| wet pellets | 770 | — | — | — |
| dry pellets | 744.25 | 2.58 | 0.56 | 34.9 |

An Angle of repose below 50° (34.9) indicates that Pellet Feed 3 has good flowability. The bulk density indicates that the particles can be compacted, if desired.

TABLE 5

Pellet Feed 3: Particle Size Analysis

| Mesh # | Size Retained (microns) | Amount Retained (g) | percent Retained |
|---|---|---|---|
| 20 | 840 | 6.4 | 12.7 |
| 30 | 600 | 14.1 | 27.9 |
| 40 | 420 | 14.8 | 29.3 |
| 60 | 250 | 9.5 | 18.8 |
| 80 | 177 | 3.5 | 6.9 |
| 100 | 150 | 1.7 | 3.4 |
| Pan | <150 | 0.5 | 1.0 |
| Total | — | 50.5 | — |

The particle size analysis for Feed 3 indicates that about 88.7% of the particles are greater than 60 mesh, whereas about 69.9% of the particles are greater than 40 mesh or about 69.9%>0.4 mm.

Then Feed 3 beads were evaluated in cell viability, growth and performance (protein titer) assays just like Feed 2. Feed 3 pellet/beads results were compared to liquid supplement (the positive control; that is, Thermo Fisher Catalog # PL002616P1 reconstituted in liquid and sterile filtered before use). For the assays, DG44-IgG cell line was grown in CD-CHO medium (Thermo Fisher Catalogue #12490), just like Feed 2 (Feed 2 pellet=Pelletization trial 1; Feed 3 pellet=Pelletization trial 2). Cells were sub-passaged three times for 3 days, and with each sub-passage, cells were split into $3 \times 10 \, e^5$ viable cells/ml. At the $4^{th}$ sub-passage, daily cell counts were taken.

Automated Feed 3 pellet/beads were compared to liquid supplement (the positive control) in cell growth assays—FIG. 4C. Cell culture supplemented with Pellet Feed 3 showed comparable cell growth to positive control over a period of 14 days in culture, especially as compared to negative control (day 7 onwards). Pellet Feed 3 showed viable cell counts ~$9 \times 10 \, e^6$ cells/ml (growth) slightly higher than cell culture supplemented with Positive Control Feed (~$8 \times 10 \, e^6$).

Viability assays were performed for Pellet Feeds 3 and compared to positive (with liquid feed supplementation) or negative controls (no liquid or pellet supplementation)—FIG. 7A. As seen from the graphs in 7A, Feeds 2, 3 compared well, like the positive control and were better than the negative control, especially after day 6.

Cell performance (antibody production) assays were performed for Pellet Feeds 2, 3 and 4 and compared to positive (with liquid feed supplementation) or negative controls (no liquid or pellet supplementation))—FIG. 7B. As seen from the graph, Feed 3 compared well, like the positive control and better than the negative control, especially after day 4. Cell culture supplemented with Pellet Feed 3 (~243 µg/ml) showed IgG production slightly higher than the Positive Control Feed; the un-supplemented cell culture assay (negative control) showed much lower IgG (~100 µg/ml) when compared with cell culture supplemented with any Pellet Feed 3.

Example 8: Fluid Bed Automatic Pelletization Using Rotor Technology—Production of Pellet Feed 4

Feed 4 pellets/beads were prepared in an automated process as described below.
1. Started with milled dry base powder (not granulated) Thermo Fisher Catalog # PL002616P1—600.0 g (Net Weight) blended with a binder, for e.g.: Avicel® Microcrystalline Cellulose, (400.0 g Net Weight) FMC BioPolymer Type PH-101, Lot No. P114826548.
2. Loaded the blended powder into a fluid bed processor equipped with a rotor disc.
7. Turn-on fluid bed processor to pre-set conditions (identified during development runs) to begin direct pelletization from powder. (e.g., air volume, atomization air pressure flow rate, inlet temperature, outlet temperature, product temperature, solvent spray rate, rotor disk speed, disk gap, disk shape etc.)
3. Monitor pellet formation by taking in-process sample measurements (e.g., microscopy FIG. 5A; other physical properties=Table 6; analytics; particle size FIG. 5B and Table 7 below) to determine when process is complete.
4. Discharge wet pellets (824.1 g Total Weight) from fluid bed processor.
5. Dry the wet pellets perform physical properties analysis (Table 6).
6. Remove approximately 50.0 g of pellets for particle size measurement (Table 7).

TABLE 6

Pellet Feed 4: Physical Characteristics

| Material | Weight (g) | Loss on drying (%) | bulk density (g/cc) | Angle of Repose |
|---|---|---|---|---|
| milled powder | 950 | — | 0.719 | 37.8 |
| wet pellets | 824.1 | — | — | — |
| dry pellets | 788.1 | 4.37 | 0.5 | 43 |

An Angle of repose below 50° (43) indicates that Pellet Feed 4 has good flowability. The bulk density indicates that the particles can be compacted, if desired.

TABLE 7

Pellet Feed 4: Particle Size Analysis

| Mesh # | Size Retained (microns) | Amount Retained (g) | percent Retained |
|---|---|---|---|
| 20 | 840 | 2.9 | 5.8 |
| 30 | 600 | 1 | 2.0 |
| 40 | 420 | 2.6 | 5.2 |
| 60 | 250 | 12.7 | 25.5 |
| 80 | 177 | 17.1 | 34.3 |
| 100 | 150 | 13 | 26.1 |
| Pan | <150 | 0.5 | 1.0 |
| Total | — | 49.8 | — |

The particle size analysis for Feed 4 indicates that only about 38.5% of the particles are greater than 60 mesh, whereas only about 15% of the particles are greater than 40 mesh or only about 15%>0.4 mm. The spread of particle size was greater and more particles were of smaller particle size.

Then Feed 4 beads were evaluated in cell viability, growth and performance (protein titer) assays just like Feed 2 and Feed 3. Feed 4 pellet/beads results were compared to liquid supplement (the positive control; that is, Thermo Fisher Catalog # PL002616P1 reconstituted in liquid and sterile filtered before use). For the assays, DG44-IgG cell line was grown in CD-CHO medium (Thermo Fisher Catalogue #12490). Cells were sub-passaged three times for 3 days, and with each sub-passage, cells were split into $3 \times 10 \, e^5$ viable cells/ml. At the $4^{th}$ sub-passage, daily cell counts were taken.

Automated Feed 4 pellet/beads comprising additional binder (crystalline cellulose) were compared to liquid supplement (the positive control) in cell growth assays—FIG. 5C. Cell culture supplemented with Pellet Feed 4 showed comparable cell growth to positive control over a period of 14 days in culture, especially as compared to negative control (day 7 onwards).

Viability assays were performed for Pellet Feeds 4 and compared to positive (with liquid feed supplementation) or negative controls (no liquid or pellet supplementation)—FIG. 7A. As seen from the graphs in 7A, Feeds 2, 3 and 4 compared well, like the positive control and better than the negative control, especially after day 6.

Cell performance (antibody production) assays were performed for Pellet Feed 4 (comprising binder cellulose) and compared to positive (with liquid feed supplementation) or negative controls (no liquid or pellet supplementation)—FIG. 7B. As seen from the graph, Feed 4 compared well, just like the positive control and significantly better than the negative control, especially after day 4. Cell culture supplemented with Pellet Feed 4 (~200 µg/ml) showed IgG production slightly lower but comparable to the Positive Control Feed; meanwhile the un-supplemented cell culture assay (negative control) showed much lower IgG (~100 µg/ml) when compared with cell culture supplemented with any Pellet Feed 4.

Example 9: Fluid Bed Automatic Pelletization Using Rotor Technology—Production of Pellet Feed 5

Feed 5 pellets/beads were prepared in an automated process as described below.
1. Started with micronized dry base powder Thermo Fisher Catalog # PL002616P1—950.0 g (Net Weight).
2. Loaded the powder into a fluid bed processor equipped with a rotor disc.
3. Turn-on fluid bed processor to pre-set conditions (identified during development runs) to begin direct pelletization from powder. (e.g., air volume, atomization air pressure flow rate, inlet temperature, outlet temperature, product temperature, solvent spray rate, rotor disk speed, disk gap, disk shape etc.)
4. Monitor pellet formation by taking in-process sample measurements (e.g., microscopy FIG. 6A; other physical properties=Table 8; particle size FIG. 6B and Table 9 below) to determine when process is complete.
5. Discharge wet pellets (824.1 g Total Weight) from fluid bed processor.
6. Dry the wet pellets perform physical properties analysis (Table 8).
7. Remove approximately 50.0 g of pellets for particle size measurement (Table 9).

TABLE 8

Pellet Feed 5: Physical Characteristics

| Material | Weight (g) | Loss on drying (%) | bulk density (g/cc) | Angle of Repose |
|---|---|---|---|---|
| milled powder | 950 | — | 0.719 | 37.8 |
| wet pellets | 728.8 | — | — | — |
| dry pellets | 716.2 | 3.31 | 0.57 | 34.9 |

An Angle of repose below 50° (34.9) indicates that Pellet Feed 5 has good flowability. The bulk density indicates that the particles can be compacted, if desired.

TABLE 9

Pellet Feed 5: Particle Size Analysis

| Mesh # | Size Retained (microns) | Amount Retained (g) | percent Retained |
|---|---|---|---|
| 20 | 840 | 4.4 | 8.8 |
| 30 | 600 | 1.1 | 2.2 |
| 40 | 420 | 8.1 | 16.3 |
| 60 | 250 | 28.1 | 56.4 |
| 80 | 177 | 6.4 | 12.9 |
| 100 | 150 | 0.3 | 0.6 |
| Pan | <150 | 1.4 | 2.8 |
| Total | — | 49.8 | — |

The particle size analysis for Feed 5 indicates that about 83.7% of the particles are greater than 60 mesh, whereas about 27.3% of the particles are greater than 40 mesh or about 27.3%>0.4 mm.

Then Feed 5 beads were evaluated in cell viability, growth and performance (protein titer) assays just like Feed 2, 3, 4 (data not shown). For the assays, DG44-IgG cell line was grown in CD-CHO medium (Thermo Fisher Catalogue #12490). Cells were sub-passaged three times for 3 days, and with each sub-passage, cells were split into $3\times10~e^5$ viable cells/ml. At the $4^{th}$ sub-passage, daily cell counts were taken. Feed 5 pellet/beads results were compared to liquid supplement (the positive control: Thermo Fisher Catalog # PL002616P1 reconstituted in liquid and sterile filtered before use).

Cell culture supplemented with Pellet Feed 5 yielded similar cell growth assays, cell viability assays, cell performance (antibody production) assays like positive control over a period of 14 days in culture, similar to results like Feeds 2, 3 and 4 (data not shown).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of making a cell culture medium pellet, the method comprising:
   a) introducing into a spinning disc rotor of a fluid bed apparatus a first dry cell culture medium powder comprising a basal medium, a complete medium, a feed, a supplement, a medium concentrate, a feed concentrate, or an amino acid mixture that can support the cultivation of a cell in culture;
   b) introducing into the spinning disc rotor of step (a) a solvent and/or a second dry cell culture medium comprising a basal medium, a complete medium, a feed, a supplement, a medium concentrate, a feed concentrate, or an amino acid mixture that can support the cultivation of a cell in culture, such that the cell culture medium pellet is formed; and
   c) drying the cell culture medium pellet,
   wherein the first dry cell culture medium powder, the second dry cell culture medium powder, or the solvent comprises a binder, an excipient, or both.

2. The method of making the cell culture medium pellet of claim 1, wherein the first dry cell culture medium powder of step (a) is pre-wetted, and optionally, no solvent is introduced in step (b).

3. The method of making the cell culture medium pellet of claim 1, wherein the first and second dry cell culture medium powders are either the same type of dry cell culture medium powders or different type of dry cell culture medium powders.

4. The method of making cell culture medium pellet of claim 1, wherein the binder or the excipient is selected from the group consisting of a sugar, a natural substance, a synthetic substance and a semisynthetic substance.

5. The method of making the cell culture medium pellet of claim 4, wherein the sugar is selected from the group consisting of glucose, sucrose, trehelose, a monosaccharide, a disaccharide and an oligosaccharide, and wherein the natural substance is a microcrystalline cellulose.

6. The method of making the cell culture medium pellet of claim 5, wherein the amount of glucose in the pellet is from about 0.1% to about 100% by mass.

7. The method of making the cell culture medium pellet of claim 1, wherein said pellet size is about 0.05 mm to about 7 mm.

8. The method of making the cell culture medium of claim 1, wherein, the disc rotor spins at variable speeds.

9. The method of making the cell culture medium pellet of claim 1, wherein the solvent is introduced in step (b) through a tangential spray, a top spray, or a bottom spray.

10. The method of making the cell culture medium pellet of medium of claim 1, wherein the rate of the solvent introduced in step (b) is between about 1 gm/min up to about 30 gm/min.

11. The method of making the cell culture medium pellet of claim 10, wherein the rate of the solvent introduced in step (b) is about 5 gm/min.

12. The method of making the cell culture medium pellet of medium of claim 1, wherein a temperature of an inlet gas is at about 20° C. to 30° C.

13. The method of making the pelletized cell culture medium of claim 1, wherein said pellet size is about 0.05 mm to about 0.5 mm, or about 0.05 mm to about 1 mm, or about 0.05 mm to about 2 mm, or about 0.05 mm to about 3 mm, or about 0.05 mm to about 4 mm, or about 0.05 mm to about 5 mm, or about 0.05 mm to about 6 mm, or about 0.05 mm to about 0.1 mm, or about 0.05 mm to about 0.2 mm, or about 0.05 mm to about 0.3 mm, or about 0.05 mm to about 0.4 mm, or about 0.1 mm to about 1 mm, or about 0.1 mm to about 2 mm, or about 0.1 mm to about 3 mm, or about 0.1 mm to about 4 mm, or about 0.1 mm to about 5 mm, or about 0.1 mm to about 6 mm, or about 0.5 mm to about 1 mm, or about 0.5 mm to about 2 mm, or about 0.5 mm to about 3 mm, or about 0.5 mm to about 4 mm, or about 0.5 mm to about 5 mm, or about 0.5 mm to about 6 mm, or about 0.5 mm to about 7 mm, or about 1 mm to about 2 mm, or about 1 mm to about 3 mm, or about 1 mm to about 4 mm, or about 1 mm to about 5 mm, or about 1 mm to about 6 mm, or about 1 mm to about 7 mm.

14. The method of making the cell culture medium pellet of claim 1, wherein a temperature for drying the pellet is about 50° C. to 60° C.

15. A method of making a base powder module pellet, the method comprising:
   a) introducing into a spinning disc rotor of a fluid bed apparatus a first nutritive media dry base powder comprising a medium base comprising one or more water soluble vitamins, one or more acid soluble vitamins, one or more neutral soluble vitamins, one or more acid soluble amino acids, one or more base soluble amino acids, one or more neutral water soluble amino acids, one or more water soluble, inorganic salts, one or more inorganic, acid soluble salts, one or more sugars, one or more acid soluble, trace elements, one or more alcohol soluble polyamines, one or more alcohol soluble lipids, and one or more buffer salts;
   b) introducing into the spinning disc rotor of step (a) a solvent and optionally, a second nutritive media dry base powder comprising a medium base comprising one or more water soluble vitamins, one or more acid soluble vitamins, one or more neutral soluble vitamins, one or more acid soluble amino acids, one or more base soluble amino acids, one or more neutral water soluble amino acids, one or more water soluble, inorganic salts, one or more inorganic, acid soluble salts, one or more sugars, one or more acid soluble, trace elements, one or more alcohol soluble polyamines, one or more alcohol soluble lipids, and one or more buffer salts, such that a pellet of the base powder module is formed; and
   c) drying the base powder module pellet,
   wherein the first dry base powder, the second dry base powder, or the solvent comprises a binder, an excipient, or both.

16. The method of making the nutritive media base powder module pellet of claim 15, wherein the base powder comprises by mass 25-40% amino acids, 20-65% D-glucose, 1-5% vitamins, 2-10% salts, and 0.01-0.05% trace components.

17. The method of making the nutritive media base powder module pellet of claim 15, wherein the base powder comprises by mass 31-32% amino acids, 59-60% D-glucose, 25% vitamins, 6-7% salts, and 0.01-0.05% trace components.

18. A method of producing a nutritive medium pellet, a nutritive medium supplement pellet, a nutritive medium subgroup pellet or a buffer pellet, the method comprising:
   (a) introducing into a spinning disc rotor of a fluid bed apparatus a dry powder medium, a supplement, a medium subgroup, or a medium buffer;
   (b) introducing a solvent and/or a second dry powder medium, supplement, medium subgroup, or medium buffer; and
   (c) forming a pellet, wherein the pellet comprises a binder or excipient.

19. The method of making the nutritive medium pellet, a nutritive medium supplement pellet, a nutritive medium subgroup pellet or a buffer pellet of claim 18, wherein the binder is D-glucose.

* * * * *

UNITED STATES PATENT AND TRADEMARK OFFICE
CERTIFICATE OF CORRECTION

PATENT NO. : 10,822,584 B2
APPLICATION NO. : 15/566899
DATED : November 3, 2020
INVENTOR(S) : Phelps et al.

Page 1 of 1

It is certified that error appears in the above-identified patent and that said Letters Patent is hereby corrected as shown below:

In the Claims

In Column 29, Claim 4, Line 13, delete "semisynthetic" and insert --semi-synthetic--, therefor.

In Column 29, Claim 5, Line 16, delete "trehelose" and insert --trehalose--, therefor.

In Column 29, Claim 8, Line 26, delete "wherein, the" and insert --wherein the--, therefor.

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*